(12) United States Patent
Jain et al.

(10) Patent No.: US 9,204,839 B2
(45) Date of Patent: Dec. 8, 2015

(54) MINIATURIZED IMPLANTABLE SENSOR PLATFORM HAVING MULTIPLE DEVICES AND SUB-CHIPS

(71) Applicant: Optoelectronics Systems Consulting, Inc., Storrs, CT (US)

(72) Inventors: Faquir Jain, Storrs, CT (US); Fotios Papadimitrakopoulos, West Hartford, CT (US)

(*) Notice: Subject to any disclaimer, the term of this patent is extended or adjusted under 35 U.S.C. 154(b) by 0 days.

(21) Appl. No.: 14/462,192

(22) Filed: Aug. 18, 2014

(65) Prior Publication Data

US 2014/0353791 A1    Dec. 4, 2014

Related U.S. Application Data

(63) Continuation of application No. 13/784,371, filed on Mar. 4, 2013, now Pat. No. 8,808,181.

(60) Provisional application No. 61/114,731, filed on Nov. 14, 2008.

(51) Int. Cl.

| A61B 5/00 | (2006.01) |
|---|---|
| A61B 5/1473 | (2006.01) |
| H01L 23/58 | (2006.01) |
| H01L 31/02 | (2006.01) |
| H01L 31/18 | (2006.01) |
| H01L 31/0203 | (2014.01) |
| H01L 31/048 | (2014.01) |
| H01L 23/48 | (2006.01) |

(Continued)

(52) U.S. Cl.
CPC .............. *A61B 5/6846* (2013.01); *A61B 5/0017* (2013.01); *A61B 5/1473* (2013.01); *H01L 23/481* (2013.01); *H01L 23/58* (2013.01); *H01L 31/02* (2013.01); *H01L 31/0203* (2013.01); *H01L 31/02005* (2013.01); *H01L 31/048* (2013.01); *H01L 31/18* (2013.01); *A61B 5/0031* (2013.01); *A61B 5/14532* (2013.01); *A61B 2560/0214* (2013.01); *A61B 2562/12* (2013.01); *H01L 21/02532* (2013.01); *H01L 2224/32225* (2013.01); *Y02E 10/50* (2013.01)

(58) Field of Classification Search
CPC ..................... H01L 21/02532; A61B 5/1455
USPC .................. 257/431, 432, 433, 434; 600/309
See application file for complete search history.

(56) References Cited

U.S. PATENT DOCUMENTS

| 5,625,209 A * | 4/1997 | Appleton et al. ............. 257/253 |
| 7,581,443 B2 * | 9/2009 | Kubena et al. ............. 73/504.12 |
| 2008/0154101 A1 * | 6/2008 | Jain et al. ..................... 600/309 |

*Primary Examiner* — David Vu
*Assistant Examiner* — Brandon Fox
(74) *Attorney, Agent, or Firm* — Steven M. McHugh

(57) ABSTRACT

This invention describes a hermetically sealed package which can be implanted in the body. The package comprise of stacked substrates where surface of one substrate hosts biosensors which are exposed to body fluids to monitor concentrations of substances selected from analytes, metabolites, and proteins, and body physiological parameters. The structure protects from body fluids devices that interface with the biosensor electrodes for electronic data processing, powering, and wireless communication. Biosensor electrodes are electrically connected to various electronic, optoelectronic, MEM devices using novel partial silicon vias (PSVs) that prevents leakage of body fluids. Various devices are located on different substrates which are stacked to save surface area. One of the substrate forms the cover plate which permits light for powering as well as sending receiving coded data including the analyte levels.

5 Claims, 18 Drawing Sheets

(51) Int. Cl.
*H01L 21/02* (2006.01)
*A61B 5/145* (2006.01)

Cross-sectional schematic showing a Si pillar serving as PSV realized on a SOI substrate (with no additional $SiO_2$ and poly Si layers).

Cross-sectional schematic showing two levels of Si pillar serving as PSVs realized on two SOI substrates Stacked SOI chips with multiple PSVs interconnecting various chips sealed with a cover silicon-on-sapphire substrate

MINIATURIZED IMPLANTABLE SENSOR PLATFORM HAVING MULTIPLE DEVICES AND SUB-CHIPS

CROSS REFERENCE TO RELATED APPLICATIONS

This application is a Continuation-In-Part of co-pending U.S. patent application Ser. No. 13/784,371, filed Mar. 4, 2013 and claims the benefit of U.S. patent application Ser. No. 13/784,371 and U.S. Provisional Patent Application No. 61/114,731, the contents of both of which are incorporated herein by reference in their entireties.

FIELD OF THE INVENTION

This invention relates generally to a biosensor platform and more particularly to an integrated, implantable, biosensor platform, which is sealed to permit long-term operation within a physical body.

BACKGROUND OF THE INVENTION

Implantable biosensor platforms are complex miniaturized devices that are geared to monitor the concentration of metabolites and other biochemicals in their immediate vicinity. One example of such a biosensor device is an implantable glucose sensor that can assist in the proper management of diseases, such as diabetes mellitus. In general, such biosensor platforms consist of many components in addition to the actual biosensing element. Such components typically include electronic, optoelectronic, micro-electromechanical (MEM), ultrasound and radiofrequency (RF) devices, which are configured for powering, signal processing and wireless communication operations. In the presence of moisture and oxygen, these components are particularly sensitive to corrosion and therefore should be packaged in such a way that they are impervious to their environmental elements, such as gases and body fluids. On the other hand, current electrochemical sensing element (or elements) must be in direct contact with biological fluids in order to establish operable functionality. However, in the case of extreme miniaturization, such dual environmental requirements present major fabrication issues. To complicate matters, a variety of temperature and environmentally-sensitive biomolecules should be properly deposited on these sensors and coated with a number of semi-permeable membranes and/or drug containing entities to help regulate analyte diffusion, provide biocompatibility, suppress inflammation and prevent fibrosis.

Current device packaging can be divided into two parts: (A) sub-chip assembly and (B) device passivation. In terms of sub-chip assembly, chip to chip interconnects are typically formed using: (i) through-Si-vias (TSVs), (ii) flip-chip thermo-compression and thermosonic bonding, and (iii) wire bonding in either flat or wrap-around configurations. In terms of device passivation, techniques like (i) polymer encapsulation, (ii) thermo-compression molding, and (iii) sputtering or chemical vapor deposition (CVD) growth of a variety of insulating organic and inorganic materials have been employed. Unfortunately, these techniques fail to attain the required passivation needed for devices with the aforementioned dual environmental requirements, particularly when they reach extreme miniaturization and prolonged exposure to body fluids.

For example, referring to FIG. 1 a schematic block diagram of an IC chip 300 having device packaging in accordance with the prior art is illustrated and shows a variety of interconnects along with a through-Si-via (TSV) and flip-chip bonding of two individual IC wafers. In this case, two Si wafers (1) and (2) with their respective devices (3) and (4) are shown as being electrically connected via their interconnects (6) and (8), respectively, where the electrical connection is achieved through flip-chip bonding via a bonding layer (12). The interconnects (6) and (8) are shown as being isolated by host oxide layers (5). A TSV (10), which is isolated from the top wafer (2) by insulators (7) and (9), electrically connects the back side metal layer (11) to the top wafer interconnect layer (8). Such a conventional through-Si-via (TSV) requires the formation of a hole through the entire top wafer. This is undesirable because such holes, despite their metal filling, make this packaging prone to a variety of leakages should this wafer be exposed to a corrosive environment.

SUMMARY OF THE INVENTION

A device platform is provided and includes at least one internal component, wherein the device platform is configured to isolate the at least one internal component from an environment external to the device platform while providing for electrical connectivity to at least one external component externally located on the outer surface of the device platform. The device platform also includes an enclosure, the enclosure including a top cover plate and a bottom substrate configured to define a sealed enclosure cavity for containing the at least one component, wherein the top cover plate is configured to allow reception and transmission of electromagnetic radiation, the surface of the top cover plate adjacent the enclosure cavity being covered with an epitaxial Si film in intimate cohesion, and wherein the bottom substrate is constructed of a high resistivity Si having a Si substrate material conductivity and includes at least one partial Si via (PSV), wherein the at least one partial Si via (PSV) is configured to electrically connect the at least one internal component with the at least one external component, and wherein the partial Si via (PSV) is formed by introducing a dopant with the Si material, wherein the combination of the dopant and the Si material results in at least one of a reduced conductivity and a conductivity that is opposite to that of the Si substrate material conductivity, and wherein an outer perimeter of each of the surface of the top cover plate adjacent the enclosure cavity and a surface of the bottom substrate adjacent the enclosure cavity includes a continuous gold fence cohesively bonded to its respective Si surface, wherein the top cover plate and the bottom substrate are configured such that the enclosure cavity is sealed using a gold-to-gold bond.

A method for integrating a plurality of device into a device platform is provided and includes forming the device platform using a top cover plate and a bottom substrate separated by at least one Si spacer, wherein the device platform defines a device cavity and the top cover plate is configured to allow electromagnetic radiation to be transmitted through the top cover plate, wherein a portion of the top cover plate includes an epitaxial Si film constructed from at least one of Si-on-Sapphire and Si-on-Quartz, patterning and depositing a gold film on the epitaxial Si film to create a Si—Au eutectic perimeter fence, at least one interconnect, at least one contact pad and at least one mounting pad for securing and interconnecting at least one internal component located within the device cavity, the at least one internal component including at least one of a photovoltaic cell and a photodetector, wherein the bottom substrate is constructed of a high resistivity Si substrate material, wherein the bottom substrate includes a signal processing device and a light emitting diode serving as an optical transmitter, wherein the bottom substrate includes bonding pads and interconnects deposited on a patterned insulating layer of grown or deposited oxide, wherein the bottom substrate has a plurality of partial Si vias (PSV) for electrically connecting at least one of the internal components with at least one device located on an outer surface of the bottom substrate, wherein the plurality of partial Si vias (PSVs) are electrically isolated from each other and are formed by introducing a dopant having an opposite conductivity to that of the high resistivity Si substrate, wherein the bottom substrate hosts a plurality of bottom substrate pads and the cover plate host a plurality of cover plate pads, wherein the bottom substrate pads and the cover plate pads are aligned with each other and include gold bumps of varying height to permit connectivity between components located on the cover plate and the signal processing device and the light emitting diode, wherein the Si side of the cover plate, top and bottom surfaces of the at least one Si spacer and a top side of the bottom substrate are deposited with a continuous gold fence on an outer perimeter, wherein one side of the gold fence is bonded to a Si surface forming a gold-Si eutectic mixture and wherein an opposing side of the gold fence is bonded to a like gold fence using a gold-to-gold bond to seal the device platform, A miniaturized device platform is provided and includes a first substrate and a second substrate configured to form an enclosure, the second substrate being constructed from a high-resistivity semiconductor material, wherein the miniaturized device platform is immersed in a corrosive and high temperature external environment, the enclosure housing a plurality of internal components and being configured to isolate the plurality of components from the external environment, the miniaturized device platform configured to allow reception and transmission of electromagnetic radiation through at least one of the first substrate and the second substrate, wherein the enclosure includes a plurality of partial-semiconductor-vias (PSVs) configured to electrically connect at least one of the plurality of internal components with an external component, wherein the partial-semiconductor-vias (PSemVs) are constructed on a thinned section of the second substrate and are created by introducing an impurity to the second substrate, the combination of the second substrate and the impurity configured to provide electrical conductivity, wherein the first substrate and the second substrate are cohesively sealed using a combination of at least one of an epitaxial interface, a eutectic mixture, a metal silicide, and a metal to metal bond.

A device including a layered structure in Si configured to form Si Vias for hermetically sealed electrical connectivity between two sets of devices, which are realized on at least two Si layers of a Si-on-insulator substrate, wherein the Si-on-insulator substrate is comprised of a first Si layer and a second Si layer separated by a first SiO2 layer serving as an insulator, wherein the first Si layer has on it a deposited second insulator film selected from SiO2, SiN, HfO2, and wherein Si pillars are created in the first Si layer by etching regions surrounding the Si pillars, wherein the Si pillars are supported by a first oxide layer and the second Si layer, wherein the exposed surface of the Si pillars and surrounding surface of the first Si layer are deposited with thin oxide layer selected from SiO2, HfO2, Si3N4, SiON, and wherein etched regions are filled with material selected from undoped amorphous Si, SiO2, HfO2, wherein the Si pillars have a top side and a bottom side, the bottom side interfaces with first oxide, wherein the second Si layer and the first oxide layer under the Si pillars are etched to expose the bottom side of the Si pillar in the first Si layer, wherein the exposed Si surface of bottom side of pillars are deposited with a metal providing Ohmic contact, wherein the metal is selected from gold, arsenic doped gold, aluminum, Pt, Pd, TiN, and TaN, and wherein the Ohmic contact is deposited with a metal pad selected from a biocompatible non-corrosive metal selected from Au, Pt, and Pd, and wherein the second Si layer side opposite to the first SiO2 layer is deposited with a passivation insulator layer selected from SiO2, HfO2, SiN, and Al2O3, and wherein the passivation insulator layer is patterned to expose second Si layer which is deposited with electrodes to form biosensors, electronic circuits, optoelectronic circuits, ultrasonic transducers and other devices that operate electrically, wherein the top side of the Si pillars are deposited with a metal providing Ohmic contact, and wherein the metal is selected from gold, arsenic doped gold, aluminum, Pt, Pd, TiN, and TaN, and wherein the Ohmic contact is deposited with a metal pad selected from Au, Pt, Pd, and wherein the metal pads on top side of Si pillars are connected to devices selected from electronic, photonic, optoelectronic, and micro-electro-mechanical realized in first Si layer.

A hermetically sealed structure including at least two stacks of substrates, wherein the structure permits exposure of biosensor surfaces on which electrodes are realized to monitor concentrations of substances selected from analytes, metabolites, and proteins, and body physiological parameters, wherein the structure protects from body fluids devices that interface with the biosensor electrodes for electronic data processing, powering, and wireless communication, and wherein the devices are located on any of the substrates forming a stack, wherein biosensor electrodes are electrically, connected to the devices using partial silicon vias, wherein substrates forming the stack are selected from Si, Si-on-Insulator (SOI) and Silicon-on-sapphire, silicon-on-quartz, wherein the Si-on-insulator (SOI) substrate include a first Si layer and a second Si layer separated by a first SiO2 layer severing as an insulator, wherein the Si-on-sapphire (SOS) substrate includes a Si layer on a sapphire substrate, wherein the SOS substrate serves as a cover plate permitting light energy to be used to power the solar cells, located on other substrates forming the multi-stack structure, wherein the SOS substrate cover plate permitting coded light signals to communicate with receiver photodiodes located on the Si film on the SOS or other substrates, wherein the cover plate substrate having a gold film on the Si thin film forming an eutectic, wherein the thin film having a perimeter fence formed by gold bump layer, wherein the substrate hosting the biosensor electrodes includes on its other face a perimeter gold fence formed on the Si—Au eutectic thin film, wherein the biosensor hosting substrate and the cover plate substrate heremetically seal the vertical stack.

DETAILED DESCRIPTION OF THE INVENTION

Figure 1:
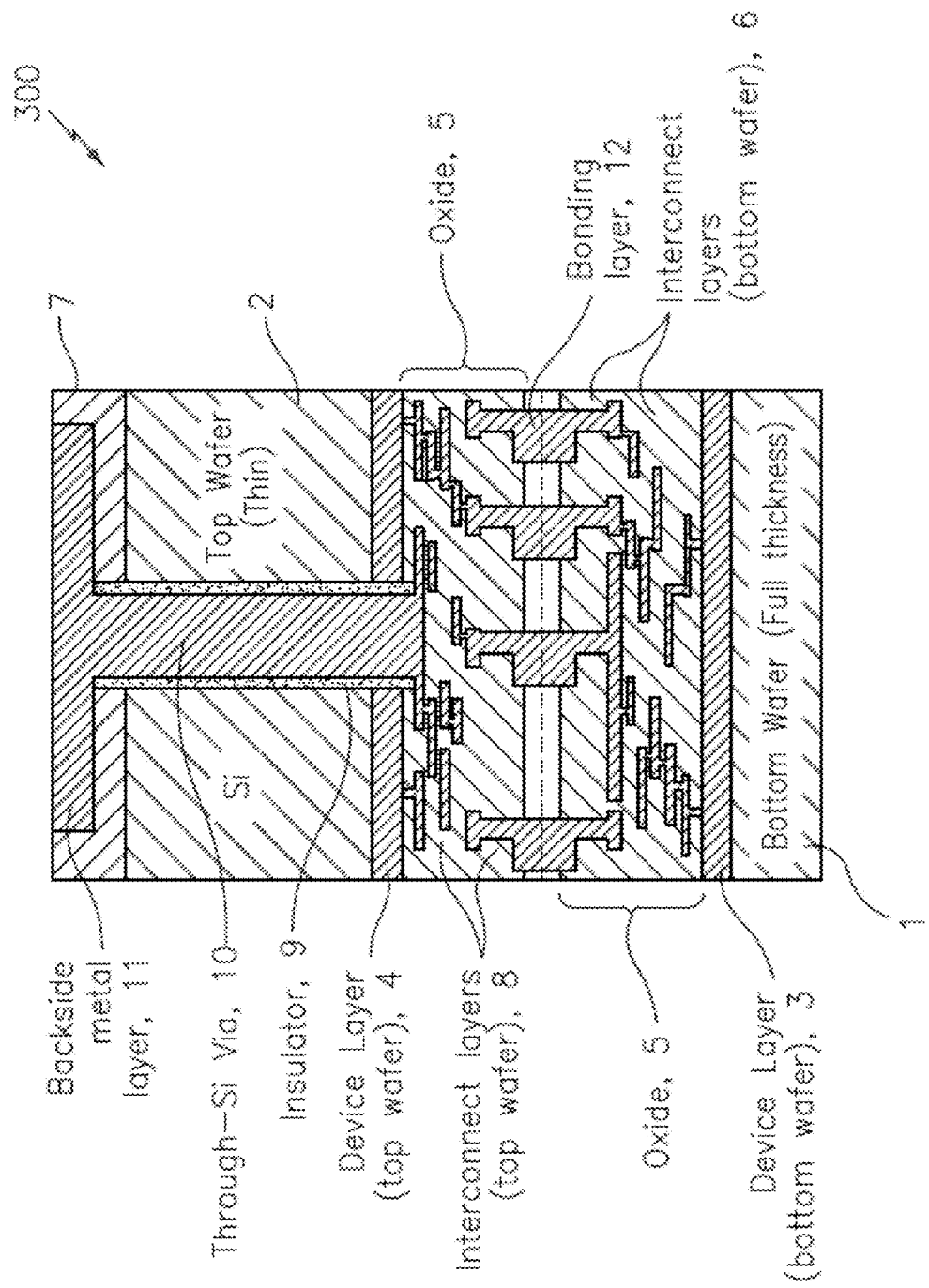
FIG. 1 is a cross-sectional view of an integrated circuit (IC) illustrating the device packaging in accordance with the prior art, where the IC includes a variety of interconnects via through-Si-via (TSV) and flip-chip bonding of two individual IC wafers.

In accordance with one embodiment of the present invention, a miniaturized, implantable, biosensor platform along with a methodology for implementing the miniaturized, implantable biosensor platform is provided. It should be appreciated that the biosensor platform may include at least one electrochemical biosensor that may be exposed to body fluids, as well as one or more sub-components that need to be hermetically sealed. Accordingly, depending on the application it is contemplated that some components and/or sub-components of the platform may need to be sealed, while other components and/or sub-components may need to be exposed. For example, when configured for use as a glucose monitor, the sensing elements need to be exposed, while the processing devices should be sealed. It is contemplated that these sub-components may come in individual sub-chips that may include electronic and optoelectronic devices as well as integrated circuits (ICs). One or more of these sub-components may interface with the electrochemical biosensors and may be configured to process their signals by converting them into a form that can be wirelessly transmitted via optical, ultrasound and/or radio frequency (RF) waves to an external unit. In addition, a variety of powering devices may be included with these sub-components and may include, but are not limited to, photovoltaic (PV) solar cells, RF receivers, biofuel cells, etc.

In accordance with another embodiment, the biosensor may contain a multiplicity of two-terminal and/or three-terminal electrochemical sensors configured to detect glucose and/or other metabolite sensors (such as Lactate, oxygen, carbon dioxide, dopamine, glutamate, etc.). However, it should be appreciated that only one electrochemical sensor may be used if desired. Additionally, programmable potentiostat circuitry as well as various signal processing circuitry (such as analog-to-digital circuitry (ADC)) may be also included, where the programmable potentiostat circuitry may be used to drive the electrochemical sensors and may be configured to interface with the various signal processing circuitry. It is contemplated that the various signal processing circuitry may be integrated with existing devices or they may be provided in a separate IC chip. Additionally, the powering source for this miniaturized implantable biosensor may be based on PV solar cells, which may be integrated with existing IC's or which may be realized via a separate IC chip. This separate IC chip may also include one or more photodetectors to receive external commands in the form of optical radiation of various and different wavelengths, wherein the wavelengths may or may not be adjustable as desired. Wireless communication may be realized using a light emitting diode (LED) or laser that is interfaced with the signal processing chip. It should be appreciated that although a light emitting diode (LED) or laser is disclosed herein with regards to realizing the wireless communication, any RF frequency suitable to the desired end purpose may be used.

Moreover, due to the corrosive nature of body fluids, these sub-chips should be hermetically packaged within a miniaturized enclosure (which may also be sealed), which is in operable electrical communication with the subcutaneous, body-fluid-immersed electrochemical sensing element. In accordance with the invention, such packaging methodology provides for a biosensor platform that is robust enough to exclude oxygen and body fluids from its internal cavity for extended periods of time (i.e. few months to few years). Moreover, the invention provides for a biosensor platform that may be extremely miniaturized so that it fits within the bore of a small diameter needle to minimize tissue damage when being inserted into a body.

Additionally, in accordance with still yet another embodiment of the invention, the invention relates generally to an implantable biosensor platform in which biosensor elements are exposed to body fluids and other devices enabling powering, biasing of sensor, and communicating with the sensors are sealed to permit long-term operation within a physical body. One of the novelties is in the implementation of interconnections between biosensor and two or more devices fabricated on various chips using Partial Si Vias (PSVs). Unlike through Si vias (TSVs) there is no complete hole which is filled. In PSVs, which seamlessly connect devices such as biosensors located on the bottom face of a sensing platform to devices on the other side. High resistivity p-Si with n-doped regions have been used to create PSVs. In the present invention, Si pillars serve as vias where the pillars are isolated by silicon oxide or other insulators that are in intimate contact and ensure no leakage of body fluid. These form also an alternate to through Si vias (TSVs).

In still yet another embodiment Si-on-insulator (SOI) substrates may be used. Moreover, SOI substrates also incorporate poly-Si layers which can be grown on Si with good adhesion. The isolated Si pillars are electrically contacted by forming Ohmic contacts, which are in turn interconnected with interconnect layers (such as gold or other suitable material) which adhere to Si when they form an eutectic. Exposed Si surfaces are deposited with SiO2 layers and etched regions are filled with amorphous Si. Ohmic contacts are interconnect materials and may be selected from gold or doped gold, platinum, palladium, nickel or other materials or combination of materials that are not attacked by body fluids.

Figure 2:
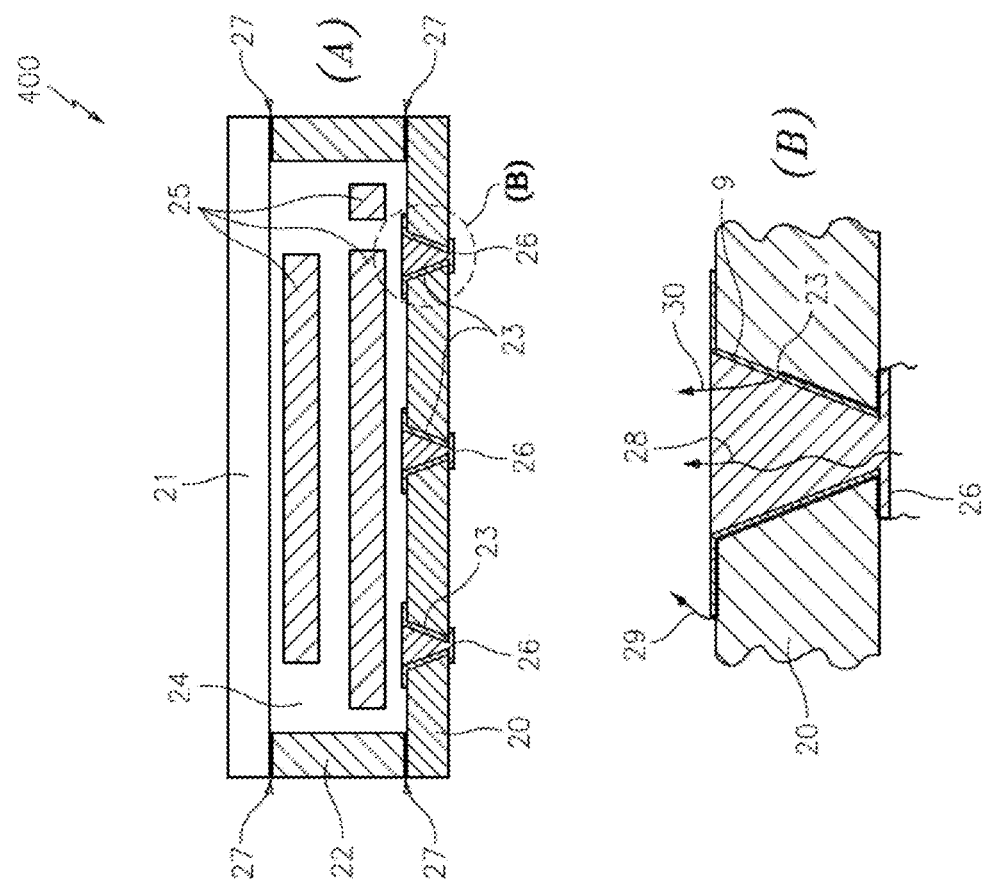
FIG. 2 is a cross-sectional view of a typical sub-chip enclosure in accordance with the prior art where the electrical interconnects have been achieved using through-Si-vias (TSVs).

Referring to FIG. 2, a cross-sectional schematic of a typical enclosure 400 in accordance with the prior art is illustrated where various components (25) of a sensor platform are housed within a sealed cavity (24), wherein the enclosure 200 includes at least one sensor terminal (26) (shown herein as having three (3) sensor terminals (26)). The cavity (24) of the enclosure 200 may be created by sandwiching at least one spacer (22) between a transparent top cover (21) and a bottom wafer (20) with a seal (27) between the spacers (22) and the transparent top cover (21) and the bottom wafer (20). The electrical connection from the inside of the enclosure 200 to the three sensor terminals (26) may be accomplished via three through-Si-vias (TSVs) (23) where the space between the TSVs (23) and the bottom wafer (20) are sealed. However, using current sealing techniques, the seals (27) and TSVs (23) of enclosure 200 are typically prone to leakage in harsh environments, such as during prolonged exposure to body fluids. The exploded view B of the TSVs (23) and sensor terminal (26) shown in FIG. 2 illustrates three possible leakage pathways associated with the TSVs, i.e. pin-hole leakage (28), as well as interface delamination (29) involving the sensor terminal (26) and/or the TSV isolation (9) along with pin-hole leakage (30) from the TSV isolation (9).

In accordance with the present invention, packaging having the desired body-fluid resistance characteristics may be accomplished by integrating some or all of the following features into the enclosure 400 of FIG. 2. Referring to FIG. 3, an enclosure 500 which integrates the features discussed hereinafter is illustrated in accordance with one embodiment of the present invention, where the features may include, i) eliminating delaminating interfaces, ii) increasing interfacial adhesion, and/or iii) eliminating through-Si-vias (TSVs) interconnects at the bottom side of the enclosure. Regarding the elimination of delaminating interfaces, prolonged exposure of layered structures to moisture and/or corrosive liquids typically results in delamination. One approach to resolve this issue involves using epitaxially grown layers (32) between two structures where little or no strain or interfacial voids can be found between the two structures. For example, interfaces between epitaxially grown Si on sapphire (SOS) and Si on quartz are of high integrity. This allows transparent top cover (21) to be integrated with a Si film, where the Si film can have its native $SiO_2$ removed from its exposed face (for example, using an HF treatment) to yield a $SiO_2$-free Si film (31).

Regarding the increase of interfacial adhesion, typically prolonged exposure of metal-semiconductor and metal-insulator interfaces to moisture and/or corrosive liquids are also prone to delamination. However, annealing evaporated Au films (33) on $SiO_2$-free Si film (31) and/or Si substrates (22) and (20) above about 363° C. in a reducing atmosphere (about 5% forming gas) followed by a gradual cooling to room temperature, forms a Au—Si eutectic mixture (34) having superior adhesion qualities. Such alloy provides a natural transition between the Si substrate and the gold deposit that is used later on to hermetically seal the structure using Au—Au seals (37), which may be attained by thermo-compression and/or thermo-sonic bonding techniques. In one embodiment, it is contemplated that the spacer (22) may have a plurality (such as two) Au/Si eutectic perimeter seals which may be mirrored on the top cover (21) and bottom substrate (20). In still another embodiment, the spacer (22) can be replaced by a gold preform or patterned foil.

Lastly, regarding the elimination of through-Si-vias (TSVs) interconnects at the bottom side of the enclosure 500, TSVs are susceptible to delamination, as well as the presence of micro-cracks and pinholes through the supporting substrate (i.e. the bottom substrate (20)). In order to achieve electrical interconnects across the bottom substrate, partial-silicon-vias (PSVs) (36) may be formed by the selective diffusion of a dopant impurity at a specified location. Since dopant diffusion requires long times to take place over a thick substrate, a partial etching (35) may be performed to make it practical. Typically, n-type impurities are diffused across a high resistivity p⁻ Si wafer, using patterned $SiO_2$ mask. The resultant n-type diffused region is surrounded by p⁻-type Si, which results in a natural electrical isolation between adjacent PSV interconnects. It should be appreciated that similar results may be obtained with diffusing p-type impurities on n-type high resistivity substrates. In an alternative embodiment, ion implanting of n-type impurities in p-substrate and subsequent thermal annealing to remove the lattice damage may also be used to achieve the desired PSVs. In another embodiment, PSV can be formed in a number of semiconductor substrates other than Si. These are termed as partial-semiconductor-vias (PSemVs). For example, semiconductor substrates like Ge, ZnSe, ZnS, SiC, etc. can be used for the formation of PSemVs.

Figure 3A:
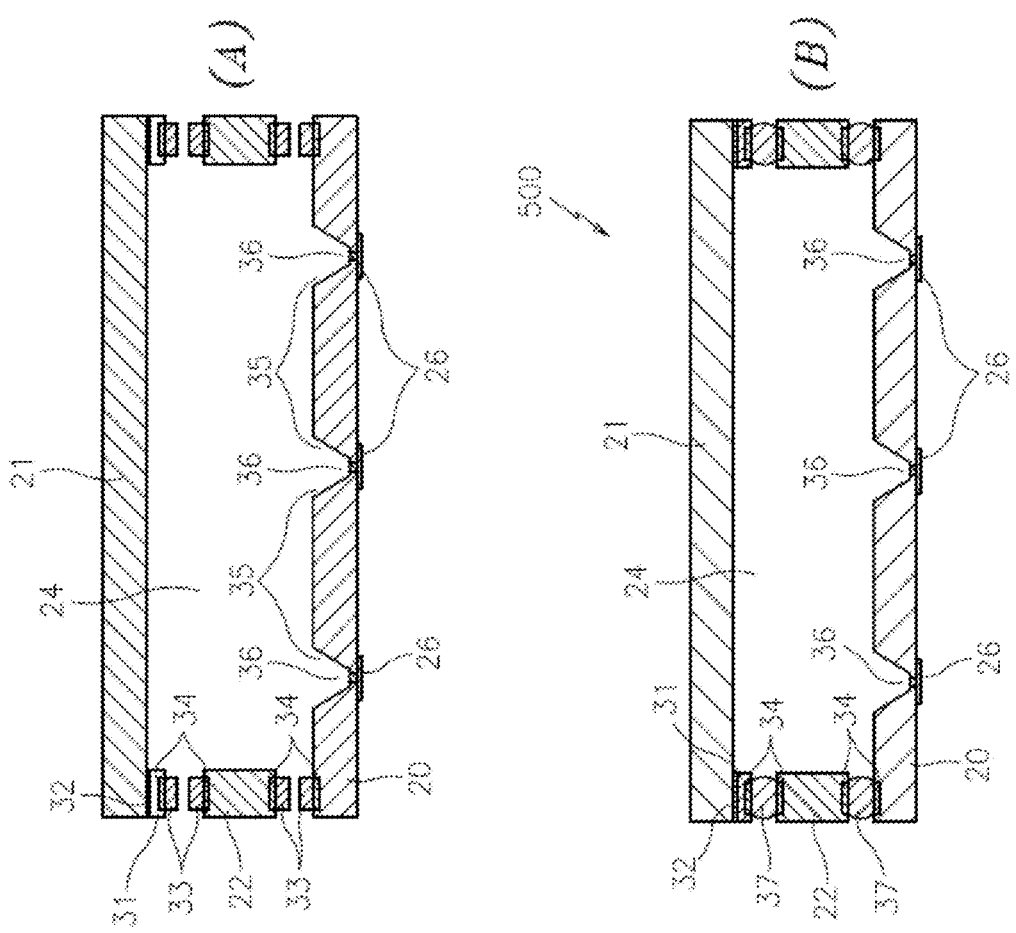
FIG. 3A is a schematic block diagram of a hermetically sealed enclosure incorporating partial-Si-vias (PSVs) along with epitaxial Si-on-insulator cover, Au/Si eutectic interfaces and Au—Au seals in accordance with the present invention.
Figure 3B:
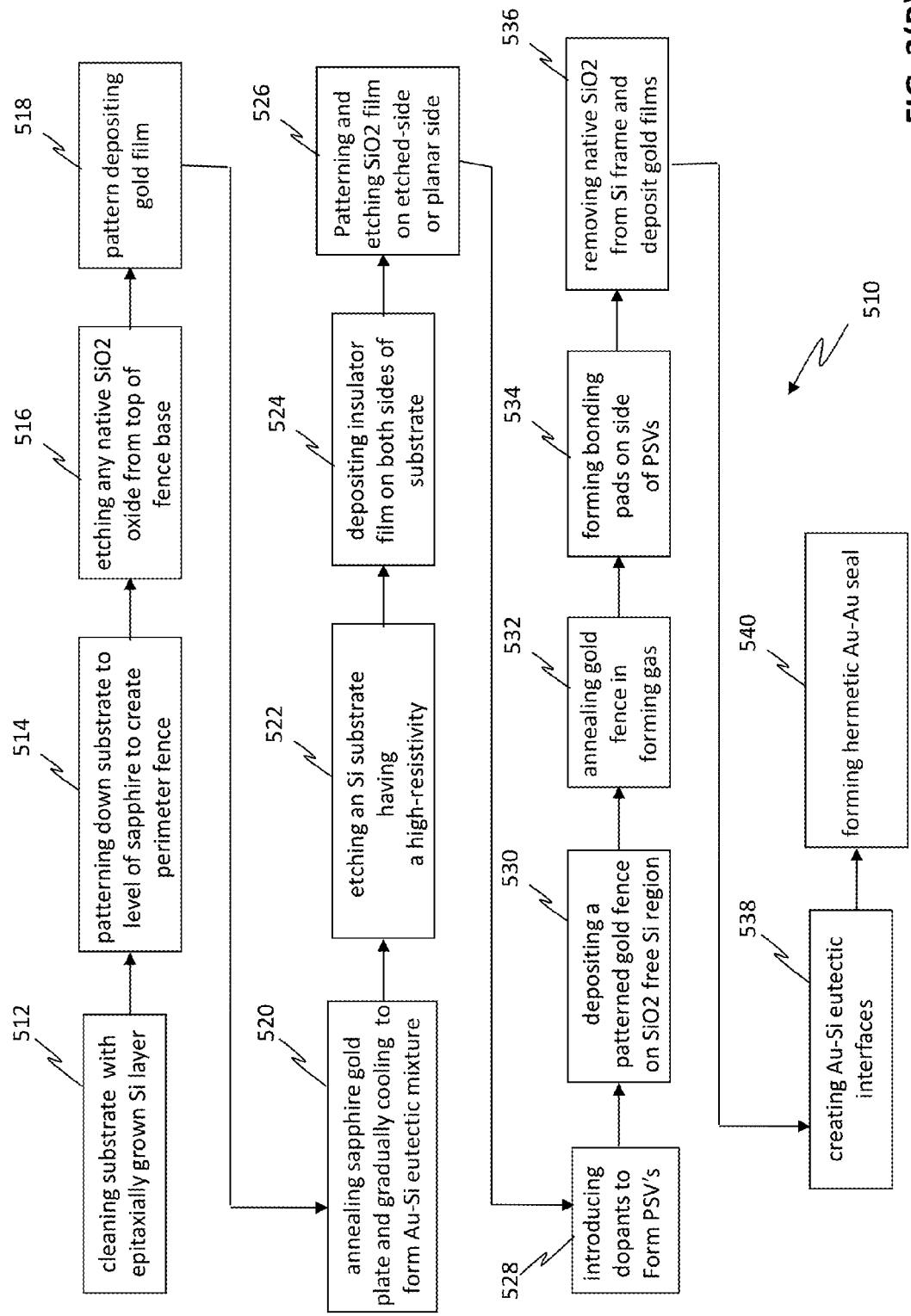
FIG. 3B is a block diagram illustrating a method for creating the enclosure of FIG. 3A.

Referring to FIG. 3B, a block diagram illustrating a method 510 for creating the enclosure 500 of FIG. 3A is provided in accordance with the present invention. Regarding the cover plate, the method 510 includes cleaning a single crystal sapphire substrate (which can be used as transparent top cover (21)) with an epitaxially grown Si layer (31) having a thickness of about 0.01 microns to about 50 microns (and more specifically, of about 0.1 microns to about 1 micron and more optimally of about 0.3 microns to about 0.5 microns), and having a robust Si-sapphire interface (32), as shown in operational block 512. The cleaned single crystal sapphire substrate (21) is patterned down to the level of sapphire to create a Si perimeter fence base, as shown in operational block 514. The method 510 includes etching any native $SiO_2$ oxide from the top of the Si perimeter fence base, as shown in operational block 516, and pattern depositing a gold film of about 0.5 microns in thickness, as shown in operational block 518. The sapphire cover plate (21) is annealed at between about 375° C. to about 400° C. in a forming gas atmosphere (for example, about 5-15% $H_2$ with the balance of $N_2$) followed by a cooling to room temperature to form a Au—Si eutectic mixture (34) possessing superior adhesion quality at the Au—Si interface, as shown in operational block 520. It should be appreciated that, if desired the gold film may be built up with additional gold layers using a variety of deposition processes such as electrochemical or electroless plating, evaporation or sputtering of Au followed by patterning, screen or ink-jet printing of gold nanoparticles, etc. If additional layers are built up, then a heat treatment step may be required to consolidate the Au deposit and remove any organics.

Regarding the high resistivity Si substrate, the method 510 includes etching a Si substrate having a resistivity in the range of about 10,000 Ω·cm, (preferably about 30,000 Ω·cm and more preferably about 60,000 Ω·cm), with either p-type or n-type doping, from one side to create etched regions (35) leaving a thin section of Si with remaining thickness in the order of about 1 micron to about 100 microns (preferably about 5 microns to about 50 microns and more preferably about 20 microns to about 30 microns), as shown in operational block 522. The method 510 includes depositing an insulator film, such as thermally grown or physically deposited $SiO_2$, on both sides of the Si substrate (not shown in FIG. 3), as shown in operational block 524. The method 510 further includes patterning and etching the $SiO_2$ film in the etched-side or the planar side to open windows for the introduction of desired dopant impurities to form electrically conducting partial-Si-vias (PSVs), as shown in operational block 526, and introducing dopant impurities to form PSVs, as shown in operational block 528. It should be appreciated that the dopant impurities may be introduced using any method suitable to the desired end purpose. For example, one method of introducing the dopant impurities involves using a diffusion furnace operating at about 1,000° C. to create PSVs (36). The duration of this introduction is commensurate to the aforementioned thickness of the thin Si section. Another method for PSV formation involves ion implantation followed by a heat treatment to remove the lattice damage. In the case of ion implantation, the deposited dopant impurities could be driven to higher depths using a high temperature (about 1,000° C. to about 1,100° C.) treatment. It should be further appreciated that the type of dopant may be chosen to be of opposite conductivity to that of the high resistivity Si substrate. For example, n-type phosphorous impurity diffusion is performed for p-type high resistivity Si substrates. In the case of n-type high resistivity Si substrates, diffusion of boron p-type impurity is performed.

The method 510 includes depositing a patterned gold perimeter fence (33) onto an SiO2-free region, as shown in operational block 530, which may be created by buffered oxide etching on the covering oxide layer of the high resistivity Si substrate (20), and annealing the gold perimeter fence in forming gas (as discussed above) to form the Au—Si eutectic interface (34), as shown in operational block 532, where the gold layer (33) can be built up to a desired thickness as discussed hereinabove. The method 510 also includes forming bonding pads (26) on one or both sides of the PSVs (36) (here only the bonding pad (26) on the planar side of the high resistivity Si substrate is shown), as shown in operational block 534. This may be accomplished by depositing a patterned Au film onto $SiO_2$-free PSV region as well as the $SiO_2$-covered portions, the latter of which may permit formation of interconnects. It should be appreciated that similarly to the perimeter fence discussed hereinabove, an annealing step in forming gas may allow the formation of ohmic contact with the PSVs. In case of n-diffused PSV regions, the gold containing trace amounts of antimony or arsenic can be used to ensure low resistivity PSV contacts.

Regarding the Si frame (22), the Si frame (22) may be created via a variety of cutting and/or etching tools as desired, such as laser machining, deep-reactive ion etching, chemical etching, ion-beam milling, ultra-sonic grinding, etc. The method 510 also includes removing the native $SiO_2$ layer on the top and bottom surfaces of the Si frame (22) and depositing gold films (33) on both sides with patterns similar to those used for fence formation on the cover plate (50) and high resistivity Si substrate (20), as shown in operational block 536. The method 510 further includes creating the Au—Si eutectic interfaces (34) via a heat treatment in forming gas, as shown in operational block 538. The method also includes aligning and sandwiching the Si frame (22) between the cover plate (21) and high resistivity Si substrate (20) and subjecting the combination to thermocompression or thermosonic bonding to form a hermetic Au—Au seal, as shown in operational block 540. It should be appreciated that such a procedure can take place in a variety of combinations as desired. For example, the cover plate (21) may first be bonded with the Si frame (22), and the high resistivity Si substrate (20) may then be bonded afterwards or vice versa.

Figure 4:
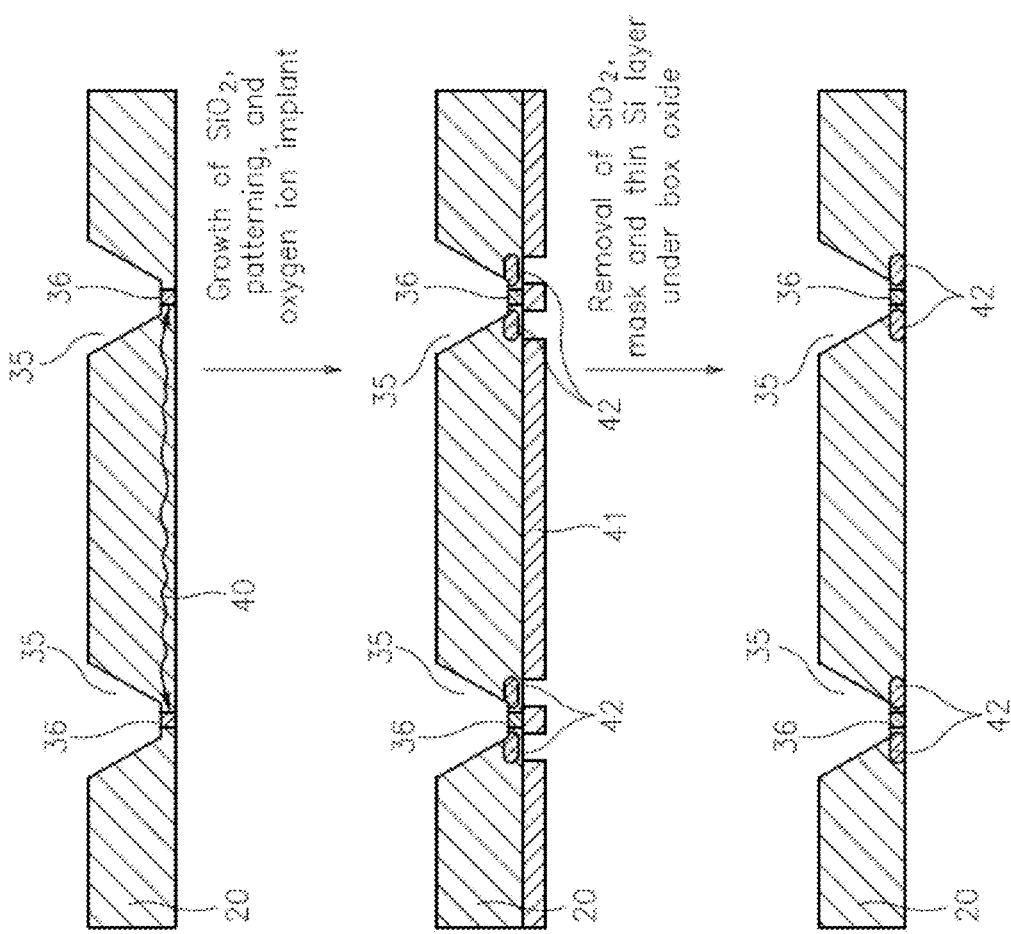
FIG. 4 is a schematic block diagram of the bottom wafer of the hermetically sealed enclosure of FIG. 3 showing the electrical isolation between adjacent partial-Si-vias (PSVs).

Referring to FIG. 4, one technique for achieving additional isolation characteristics (i.e. to eliminate possible electrical cross talk shown in (40)) between adjacent PSVs (36) is illustrated and includes using an appropriate mask (41), where oxygen implantation followed by annealing results in the formation of box oxide (42) around the PSVs (36). It should be appreciated that since the ion implantation typically penetrates over a couple of microns, the etched region (35) should have such a depth that it leaves Si regions of a few micron-thin (thick) for PSV diffusion.

Figure 5A:
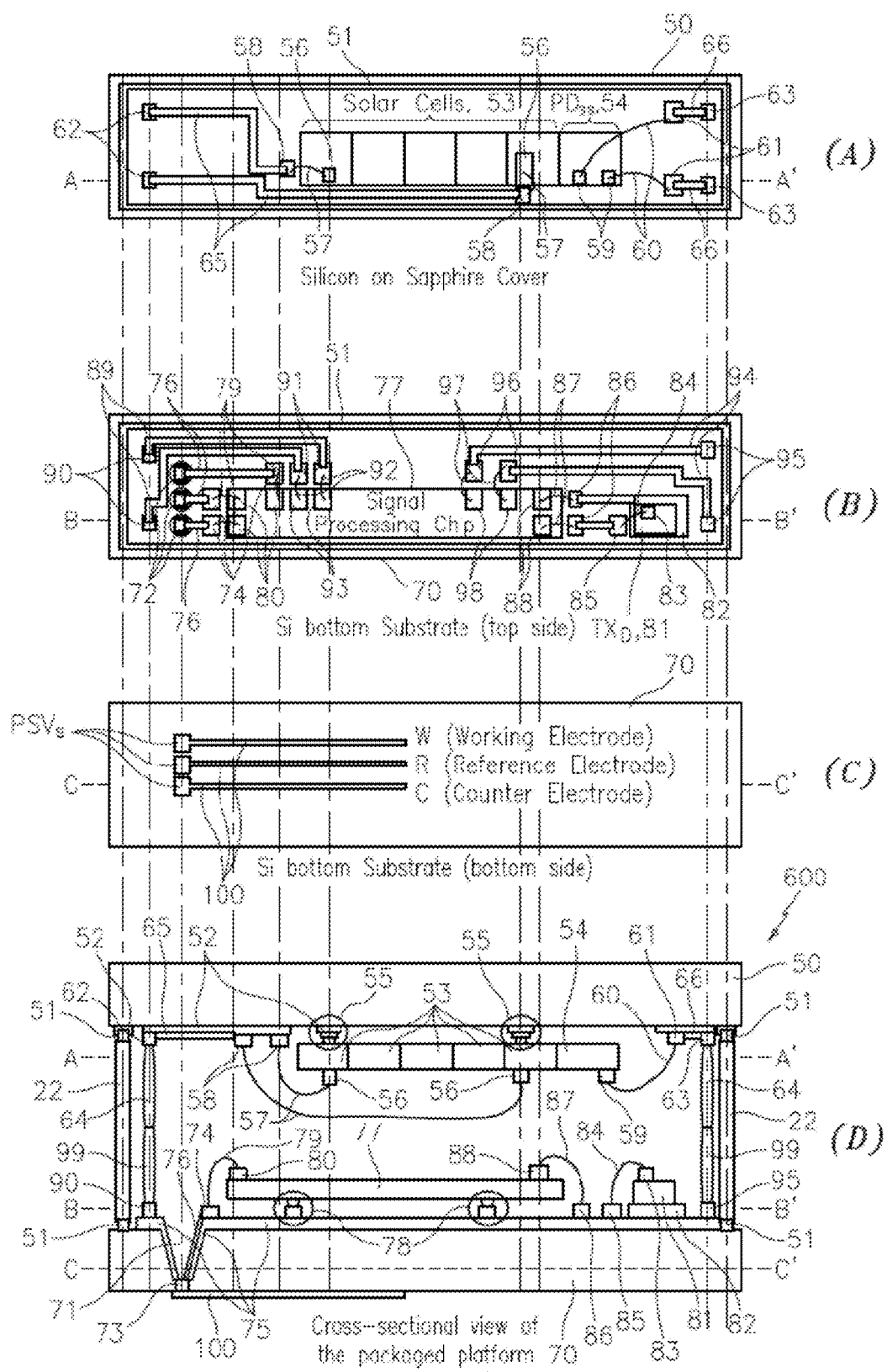
FIG. 5A is a schematic block diagram of a bio sensor platform in accordance with one embodiment of the present invention illustrating the use of wire bonding to integrate various sub-chips within a hermetically sealed enclosure.

Referring to FIGS. 5(a)-(d), the topology of an integrated biosensor platform having an enclosure 600 and using patterned interconnects and wire bonds, in accordance with the invention is illustrated. As shown in FIG. 5a, the topology of cover plate (50) (i.e. transparent top cover 21) is illustrated and includes, immediately around the perimeter of the cover plate (50), a perimeter Au fence (51) realized on a patterned Si film (52) located directly underneath (shown in FIG. 5d). This patterned Si film (52) is part of (i.e. grown on epitaxially) the cover plate (50), which may be constructed from Si-on-sapphire (SOS). The cover plate (50) includes back-illuminated solar cells (53) and photodetector $PD_{ss}$ (54), which may be mounted onto the SOS cover plate (50). It should be appreciated that although these devices (i.e. back-illuminated solar cells (53) and photodetector $PD_{ss}$ (54)) may be secured to the cover plate (50) via gold pads (55) through a Si/Au/Si eutectic (shown in FIG. 5(d)), any method or materials suitable to the desired end purpose may be used to secure these devices to the cover plate (50). It is contemplated that Mo and Moly Silicide may be used in place of gold-Si eutectic. Moreover, since Mo to Moly bond is not as low temperature as gold-gold, an intermediate material that alloys with Moly may be used in place of gold. The pads (56) on solar cells (53) may be wire bonded (57) to pads (58) which may be formed on the patterned Si film (52) on the SOS cover plate (50). Similarly the pads (58) on the $PD_{ss}$ photodetector (54) may also be wire bonded (60) to pads (61) similarly formed on the patterned Si film (52) on the SOS cover plate (50). It should be appreciated that pads (58) and (61) may be interconnected to two outer left (62) and two outer right (63) pads (where gold bump (64) is formed (See FIG. 5d)), using interconnects (65) and (66), respectively. These interconnects (65) and (66) may be formed by patterning Au deposited on either the sapphire or the patterned Si film (52) of SOS cover plate (50).

Figure 5E:
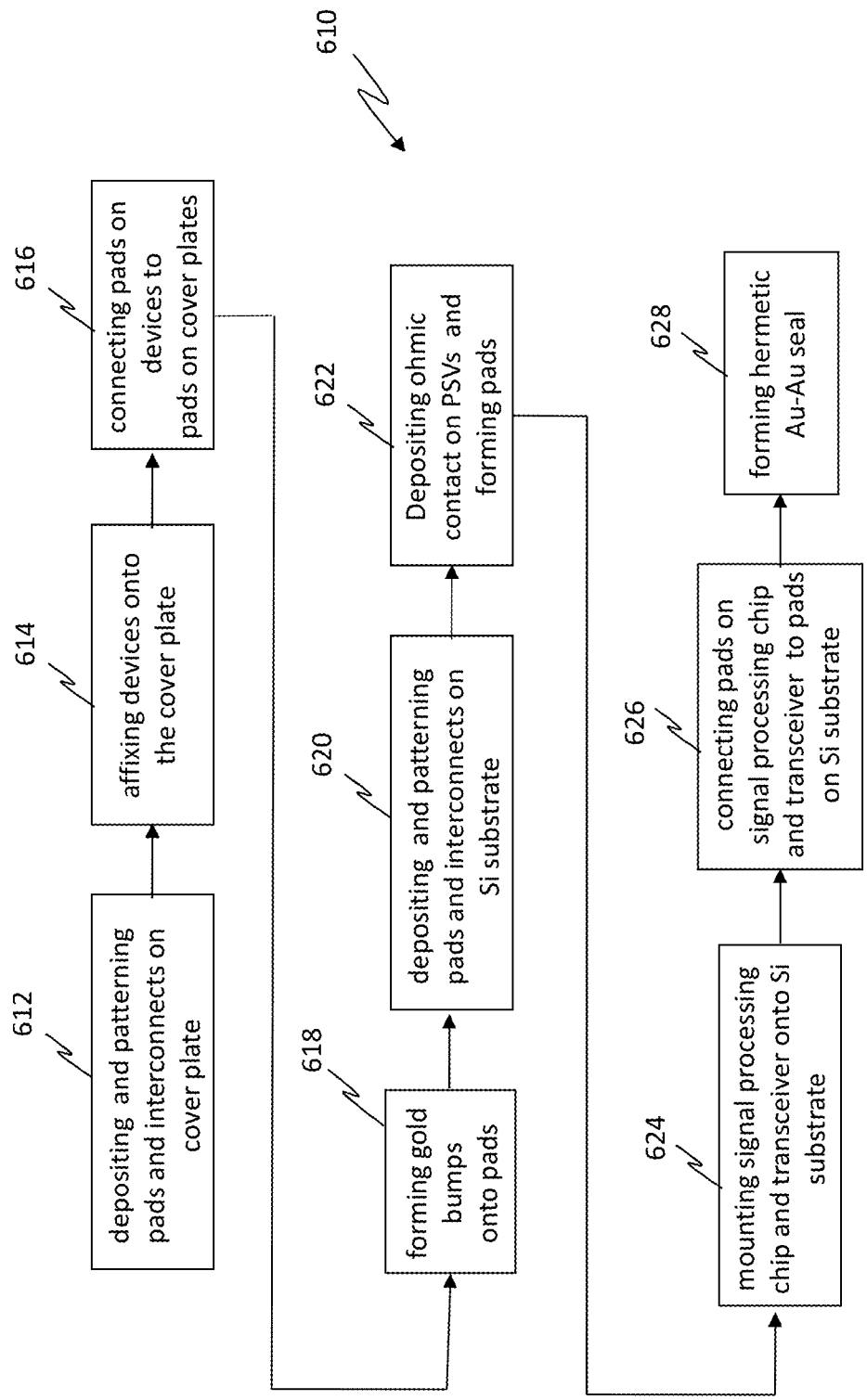
FIG. 5E is a schematic block diagram illustrating a method for creating the enclosure of FIGS. 5a-5d.

As shown in FIG. 5E, the topology of the high-resistivity bottom Si substrate (70) (i.e. bottom wafer 20) is illustrated in a similar fashion to SOS cover plate (50) and may also include a perimeter Au fence (51) immediately surrounding the perimeter of the bottom Si substrate (70). A region (71) may be etched (See FIG. 5(d)) to form at least one (in this case three) partial-Si-vias (PSVs) (72) in predetermined locations also as shown by a box (73) in FIG. 5d. As shown, three pads (74) (one for each PSV) may be formed and connected (76) with the top contact of its respective PSV. To avoid electrical crosstalk, the pads (74) as well as their interconnects (76) may be patterned on a $SiO_2$ layer (75) formed on the Si substrate (70) (shown in FIG. 5(d)). A signal processing chip (77) may be included and may be mounted onto the Si substrate (70) using Au pads (78) (shown in FIG. 5(d)). Subsequently, wire bonds (79) may be used to connect the sensor pads (74) to their equivalent pads (80) on the signal processing chip (77). In a similar fashion, the TX$_D$ LED or laser (81) may be affixed on its pad (82) and its top contact pad (83) may be wire bonded (84) to an adjacent pad (85), where the adjacent pad (85) together with pad (86) may be wire bonded (87) onto the respective pads (88) on the signal processing chip (77), where pad (86) is connected to TX$_D$ pad (82). Interconnects (89) may be configured to join the two outer left pads (90) with the pads (91), where outer pads (90) may be wire bonded (92) to the power and ground pads (93) of the signal processing chip (77). In a similar fashion, interconnects (94) may be configured to connect the two outer right pads (95) with the pads (96) which may wire bonded (97) to pads (98) on the signal processing chip (77). This affords the connection of the PDss photodetector (54), mounted on the cover plate (50) to the signal processor unit (77) located on the Si bottom substrate (70). It should be appreciated that pads (90) and (95) may be gold bumped (99) and thermo-compression bonded with the top cover bumps (64), along with the perimeter fence (51), as (shown in FIG. 5(d)). Referring to FIG. 5c, the topology of the high-resistivity bottom Si substrate (70) from the bottom side is illustrated and shows the respective PSVs (73), also shown in FIG. 5(d), that may be connected to three electrochemical electrodes (100) located on the bottom side of the high-resistivity bottom Si substrate (70).

Referring to FIG. 5E, a block diagram illustrating a method 610 for creating the enclosure 600 of FIG. 5(d) is provided in accordance with the present invention. Regarding the Si-on-sapphire cover plate (50), the method 610 includes depositing and patterning, on either pre-patterned Si regions on sapphire or Si-etched sapphire substrate or a combination of both (in FIG. 5(d) both pads and interconnects are shown to be formed onto pre-patterned Si regions), pads (62), (63), (58), (61) and (55) and interconnects (65) and (66), as shown in operational block 612. It should be appreciated that the pads (62), (63), (58), (61) and/or (55) and interconnects (65) and (66) can be made from a variety of metals (gold, aluminum, copper, etc.) and/or other conductive materials (i.e. graphene, nanotubes, heavily doped Si, conductive oxides, etc.). The method 610 further includes affixing devices (such as solar cells (53) and photodetector (PD$_{SS}$) (54)) onto the pads (55) on the cover plate (50) using any method suitable to the desired end purpose (such as flip-chip thermocompression or thermosonic bonding), as shown in operational block 614. The method 610 further includes connecting the pads on the devices (i.e. solar cells (53) and PD$_{ss}$ (54)) to the corresponding pads on the cover plate (50), as discussed above and as shown in operational block 616. It is contemplated that this may be accomplished via any method suitable as desired, such as by wire bonding. The method 610 also includes forming gold bumps (64) onto pads (62) and (63), as shown in operational block 618.

Regarding the high resistivity Si substrate (70) as shown in FIGS. 5(b)-5(d), the method 610 includes depositing and patterning pads (90), (95), (74), (91), (96), (86), (85),(82) and (78) and interconnects (65), (89) (94) and (76) onto SiO$_2$ covered substrate, as shown in operational block 620. The method 610 further includes depositing the ohmic contact (such as may be formed by gold silicon eutectic) on PSVs (73) from the etched side (71) and froming pads (72), as shown in operational block 622. It should be appreciated that this may be accomplished in accordance with the process defined hereinabove with regards to the fabrication of pads (26) in FIG. 3 and that for certain applications, pads may be formed on oxide layer deposited on silicon high resistivity substrate or directly on the substrate without any oxide underneath. The method also includes mounting the signal processing chip (77) onto pads (78) and TX$_D$ onto pad (82), as shown in operational block 624, using any method suitable to the desired end purpose, such as flip-chip bonding or other techniques. At this point, the method 610 may include connecting (using wire bonding or other acceptable method) the pads on the signal processing chip (80), (93), (98) and (88) (shown in FIG. 5(b)) and TX$_D$ (83) devices to corresponding pads on the Si substrate, as described hereinabove and as shown in operational block 626, and forming gold bumps (99) having a desired height, onto pads (90) and (95).

Regarding the Si spacer frame (22), the Si frame (22) may be created as discussed hereinabove with regards to enclosure 500 in FIG. 3. It should be appreciated that as discussed hereinabove the Si spacer (22) may be replaced by a gold preform of similar dimensions. Accordingly, the method 610 includes aligning and sandwiching the Si frame (22) between the cover plate (50) and high resistivity Si substrate (20) and subjecting the combination to thermocompression or thermosonic bonding to form a hermetic Au—Au seal, as shown in operational block 628. It should be appreciated that such a procedure can take place in a variety of combinations as desired. For example, the cover plate (50) may first be bonded with spacer (22), and the high resistivity Si substrate (20) may be bonded afterwards or vice versa. Here it should be noted that such thermocompression or thermosonic bonding procedures not only seal the perimeter fence but also allows Au—Au bonding between bumps (64) and (99) and may necessitate that the bump height be carefully controlled to afford internal electrical interconnection within the enclosure.

Figure 6:
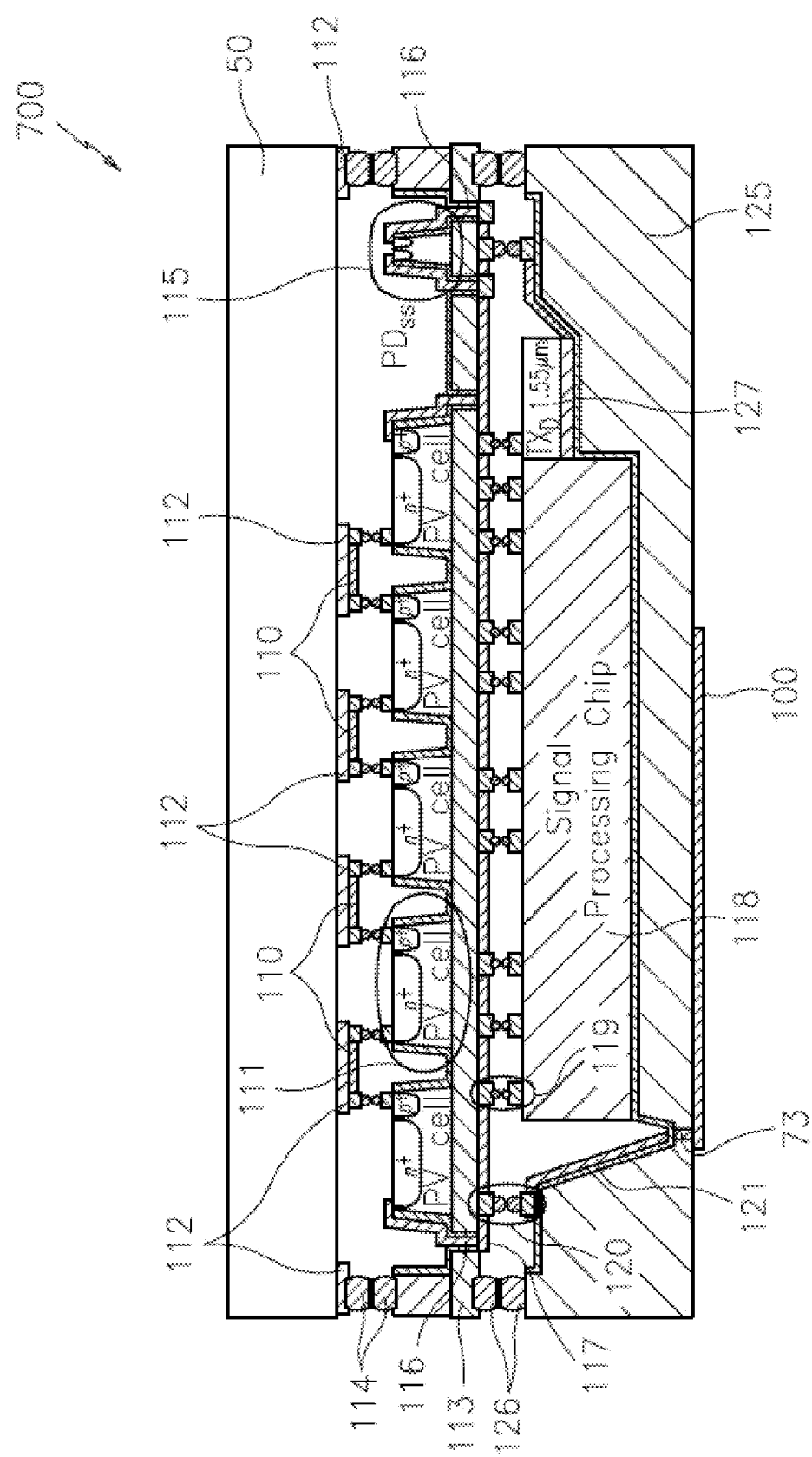
FIG. 6 is a schematic block diagram of a biosensor platform in accordance with one embodiment of the present invention using flip-chip bonding to integrate various sub-chips within a hermetically sealed enclosure.
Figure 7:
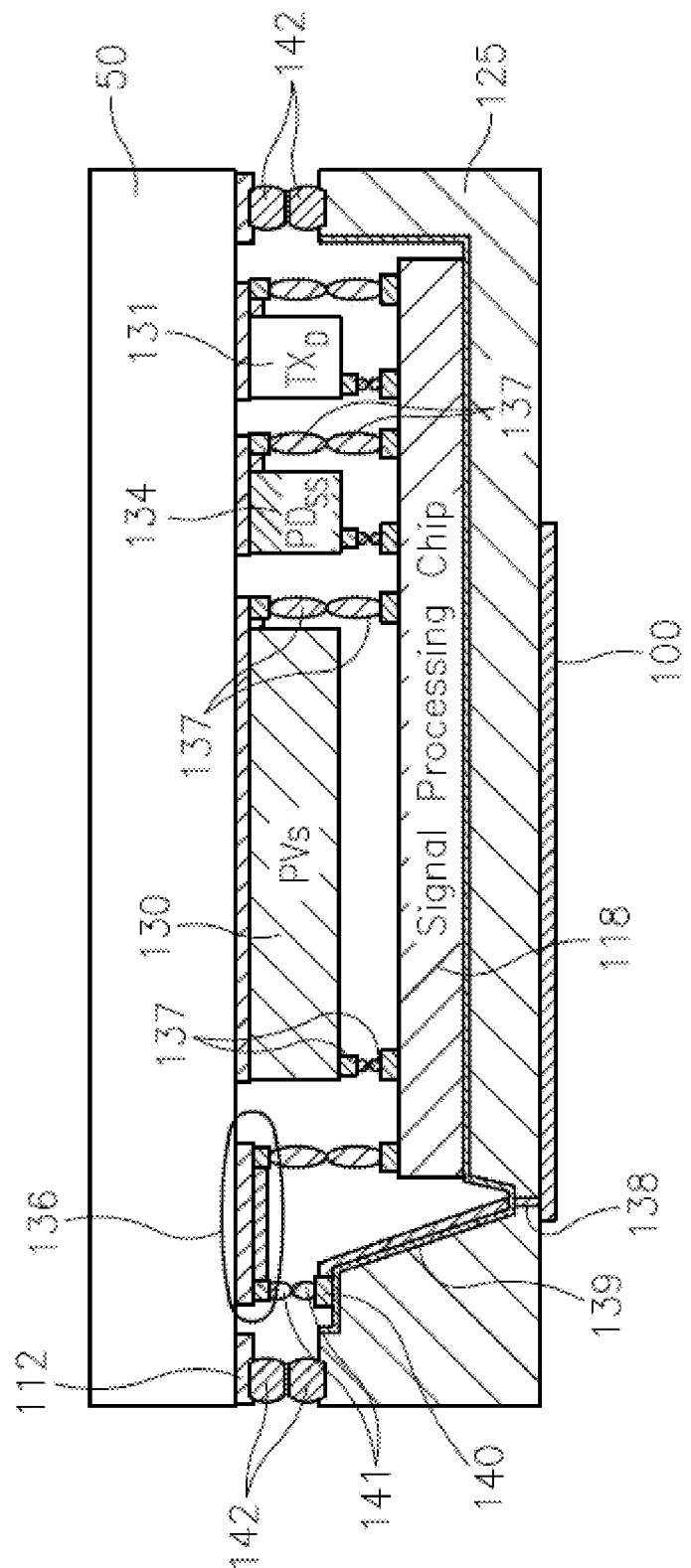
FIG. 7 is a schematic block diagram of a biosensor platform in accordance with one embodiment of the present invention using an alternate flip-chip bonding procedure to integrate various sub-chips within a hermetically sealed enclosure.

Referring to FIGS. 6 and 7, two alternate embodiments for implementing the packaged functional devices discussed herein are provided, wherein the packaged functional devices do not use wire bonding. FIG. 6 illustrates a three-layered structure, where the top SOS cover (50) may be used to provide interconnects (110) onto the various solar cells (111) of the solar array located within sealed cavity (104) and (105) of enclosure 700. The interconnects (110) may be formed on patterned Si (112) of the SOS structure (50) and the solar cells (111) may be front illuminated and front contacted and realized on a high resistivity substrate (113). The PD$_{SS}$ photodetector (115) may be of similar architecture and may also be formed on substrate (113). Thermo-compression bonding of SOS structure (50) and high resistivity substrate (113) may provide both solar cell interconnection as well as perimeter fence (114). It should be appreciated that solar and/or photodetector PD$_{SS}$ output may be provided through either PSVs or TSVs (here TSVs are shown (116) for explanation) to a distributed interconnect (117) located at the bottom side of high resistivity substrate (113). The distributed interconnect (117) may be used to direct power and PD$_{SS}$ signal to a signal processing unit (118) through any number of Au pads and bumps (119). This distributed interconnect (117) may also be used to connect the TX$_D$ LED or laser (127) that may be located on an appropriately recessed additional high resistivity substrate (125). Similarly, the distributed interconnect (117) may also be used to connect the biosensor(s) (100) to the PSVs (73) via the Au bumps and pads (120) and patterned interconnect (121). Similarly as above, thermo-compression bonding between the high resistivity substrates (113) and (125) may also provide connections for both electrical interconnection as well as acting to seal a second perimeter fence (126).

FIG. 7 illustrates a packaging structure 800 where the PV cell(s) (130), the TX$_D$ LED or laser (131), and/or the PD$_{SS}$ photodetector (134) are flip-chip mounted onto the SOS top cover plate (50). Subsequently, the appropriate height bumps (137) may be achieved using the respective contacts of the PVs (130), TX$_D$ LED or laser (131), PD$_{SS}$ photodetector (134), SOS interconnect (136) and/or the signal processing unit (118) to afford flip-chip bump-to-bump bonding and component interconnection. The composite assembly of SOS top cover plate (50) and/or signal processing unit (118) may be connected and sealed to an appropriately recessed high resistivity Si substrate (125) which contains PSVs (138), their interconnects (139), bonding pads (140), appropriate height bumps (141) and a Au/Si eutectic perimeter fence (142). In this embodiment, the height of the gold bumps (137) and (141) should be controlled to obtain an internally interconnected and sealed package platform. It should be appreciated that the gold bumps (137) or studs may be of variable heights and they connect pads which are also located at different heights. Also, the gold fence (51) formation and the gold bump interconnect realization typically occur at the same time. Accordingly, the gold bumps (137) should be fairly accurate with respect to the gold fence (51).

In an additional embodiment, the SOS top cover (50) may serve as a substrate to monolithically grow PVs (130), TX$_D$ LED or laser (131), PD$_{SS}$ photodetector (134), and/or other devices such as signal processing (118) devices. In this case, any or all of the above devices can be interconnected using a distributed interconnect placed in the high resistivity substrate (125) in the place where the signal processing chip is shown in FIG. 7 (or elsewhere as desired). This essentially involves flip-chip bonding of two wafers. In the case of the signal processing chip (118) being a separate unit, the integration may resemble that of FIG. 7. In still yet another embodiment, the top cover (50) may be constructed from a wide energy gap semiconductor material, such as GaP, ZnSe, ZnS, SiC, ZnO, etc. It should be appreciated that the band gap may be relative to the powering source (solar cells) which typically operate in the visible range (1.8 eV for 0.7 micron red light). For example, one acceptable band gap range may be between 1.8 eV-3.7 eV. These semiconductor materials can be used in place of the sapphire cover and can be epitaxially coated with a thin layer of Si to protect their outer surface from exposure to body fluids. Alternatively, a germanium (Ge) film can be used in place of Si, which also forms eutectic alloys with gold. Still yet another embodiment involves the formation of the signal processing chip (118), partial-Si-Vias (138), pads (140), interconnects (139), and/or perimeter fence (142) onto a high resistivity substrate (125), where the high resistivity substrate (125) is flip-chip bonded to the cover plate (50) and hosts all (or some) of the optical and/or optoelectronic devices.

Figure 8:
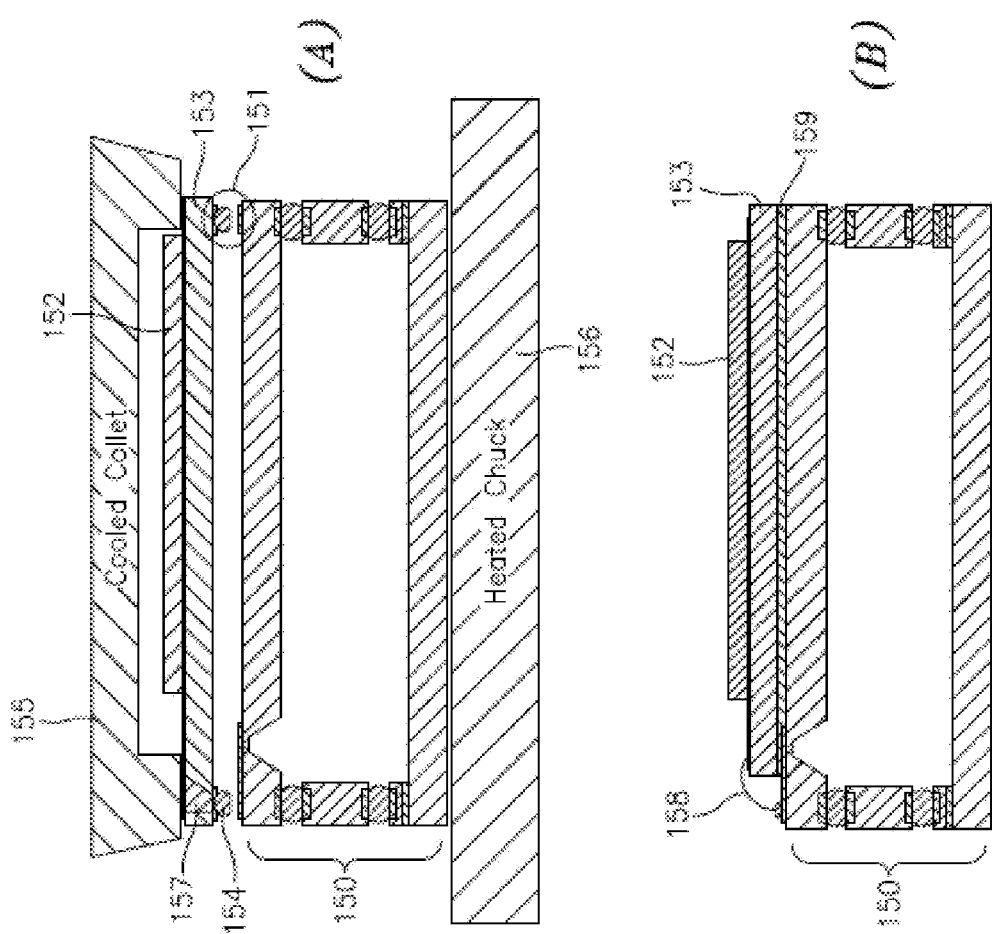
FIG. 8 is a schematic block diagram illustrating the bonding and interconnecting of a prefabricated, biosensor-containing wafer onto the integrated and hermetically sealed enclosure.

In accordance with the present invention, subsequent to packaging the electronic and optical components of the miniaturized implantable platform, appropriate coatings needed for biological detection should be deposited onto the proper components, where the coatings may typically contain a variety of proteins and hydrogels, which are temperature sensitive. Referring to FIG. 8, an embodiment where the bottom side of the packaged platform (150) is interfaced with a prefabricated biosensor (152) onto a substrate (153) is illustrated. One way to accomplish this configuration using the prefabricated biosensor (152) may involve flip-chip bonding using a cold chuck/collet (155) on the top of the package, and a heated chuck on the bottom (156) of the package (shown in FIG. 8A). It should be appreciated that the temperature range of the cold collet (155) may be about −80° C. to about 95° C. and more preferably about −40° C. to about 55° C. However, an exemplary temperature range may be about 3° C. to about 37° C. For this configuration thermo-sonic bonding may be used together with gold bumped (154) TSVs (157), where another set of dummy gold bumped pads (151) may be placed on the opposing side of the packaged platform (150) between the platform (150) and the substrate (153) of the prefabricated biosensor (152) to provide both planarity and additional adhesion. Alternatively, an ultra-sonic wire bonding (158) approach may be used together with a polymeric adhesive (159).

Figure 9:
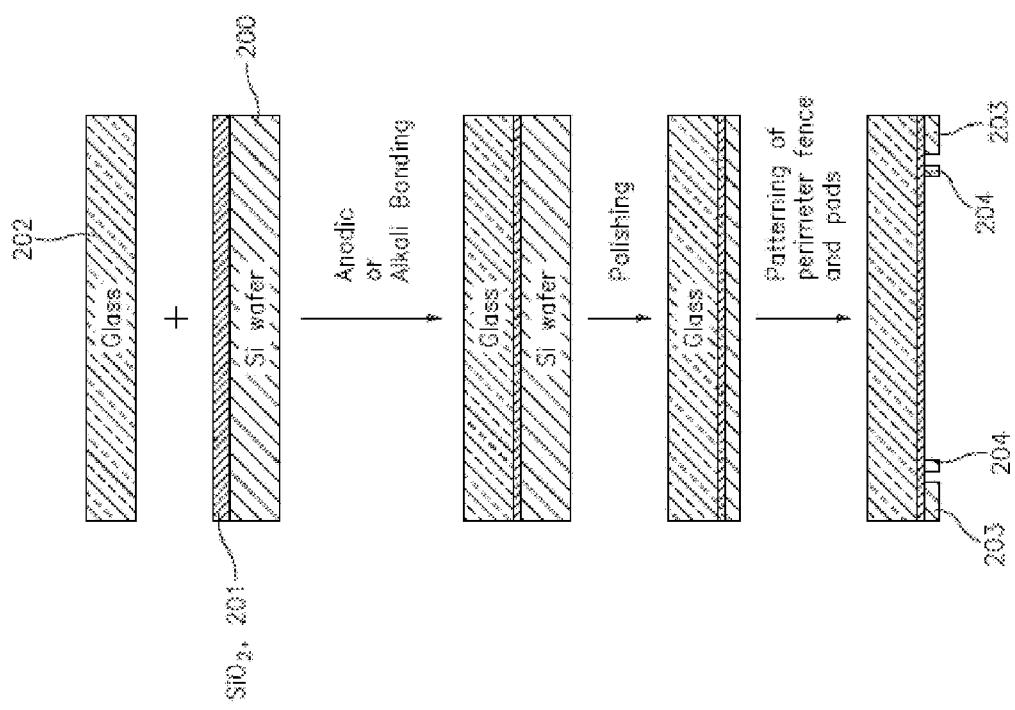
FIG. 9 is a schematic block diagram illustrating an alternative methodology to attain transparent glass covers with patterned Si films.

Referring to FIG. 9, an alternative to using epitaxial Si-on-sapphire or Si on quartz cover plates (50) is illustrated and includes using alkali or anodic bonding of a Si wafer (200), where its native oxide (201) may be bonded to a glass substrate (202). Subsequently, following wafer thinning (from the silicon side), Si patterning may permit the formation of pads (204) and a high integrity gold fence (203) as described hereinabove and as shown in FIG. 3.

Figure 10:
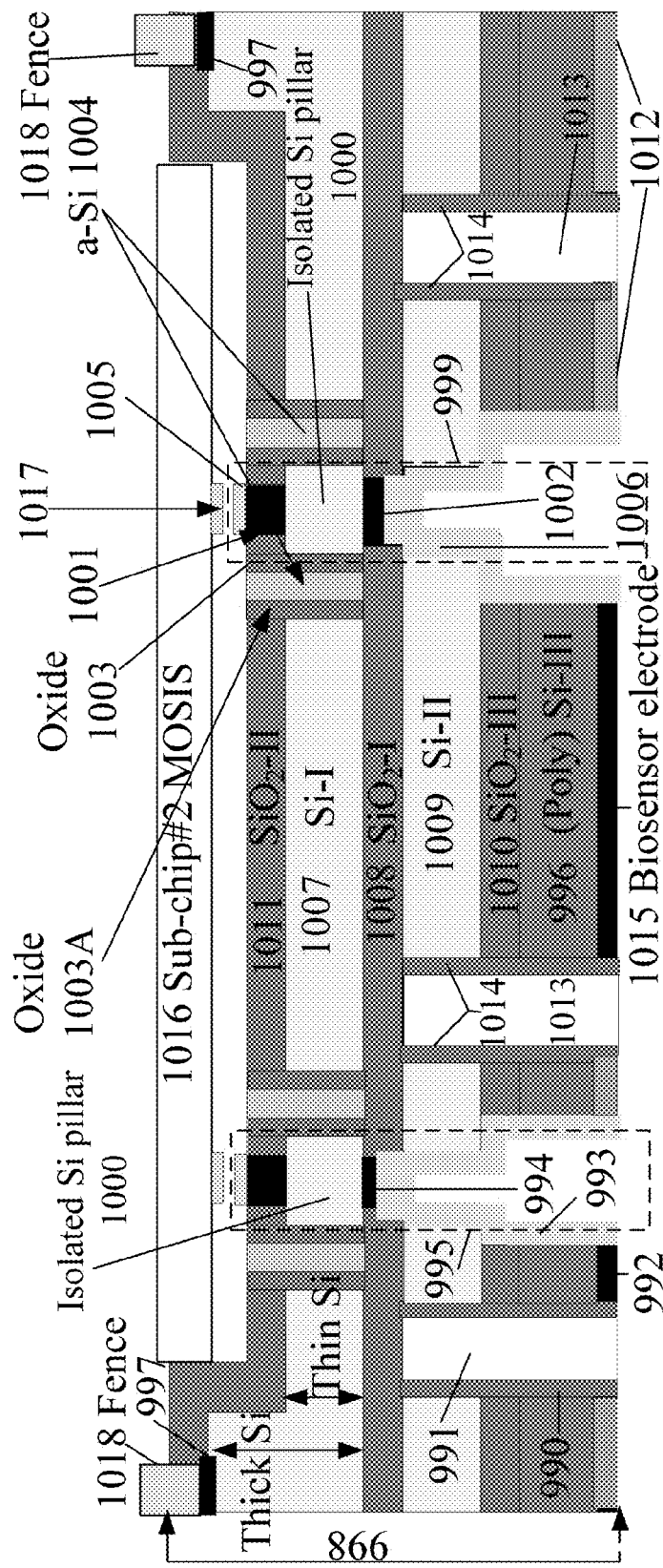
FIG. 10 is a cross-sectional schematic diagram showing Si pillars serving as partial silicon via (PSV) realized on a SOI substrate with additional $SiO_2$ and poly-Si layers.

Referring to FIG. 10, a cross-sectional schematic showing Si pillars that serve as vias realized on a SOI substrate 998 with additional SiO$_2$ III layer(s) 1010 and (poly) Si III layer(s) 996 are described. The Si III layer(s) 996 is protected by a passivation insulator layer 1012. In this version, partial Si vias 999 are created by isolating Si pillar 1000 by insulating oxide (SiO2) 1003 all around the pillar. The Si pillar 1000 is deposited with Ohmic contact 1001 on one side (the Sub-chip#2 side) and Ohmic contact 1002 from the other side (biosensor side). Ohmic contact may be realized using gold, doped gold layers (or other suitable materials) that are annealed to form an eutectic with Si. The Ohmic contacts are in turn contacted by metal pads 1005 and 1006. The SOI substrate may include a first Si layer Si-I 1007, a second Si layer Si-II 1009 separated by a first SiO2-I layer 1008. The Si-I 1007 may have an insulator layer SiO2-II 1011.

The oxide layer 1003A which is grown on Si-I layer 1007 is shown surrounding the etched region, wherein the etched region is filled with an undoped amorphous Si film 1004. The Si-I layer 1007 is shown as being thinner in the part below sub-chip#2 1016 and thicker in the part shown with perimeter fence 1018 (which may be gold). Sub-chip#2 1016 includes pads like 1017 that may be bonded (such as by flip-chip) to corresponding PSV contact pad 1005. The Ohmic contact 1001 is deposited with a gold pad 1005 and the Ohmic contact 1002 is deposited with a gold thin film 1006 to make electrical connections. Other materials may be used. Ohmic contact 1002 is created by etching SiO2-I layer 1008 which surrounds it. The gold thin film 1006 is deposited on Si-II layer 1009 and Si-III layer 996. It should be appreciated that the gold layer may have a thin chrome (Cr) layer for adhesion on SiO2-III 1010 films, if needed. The thin films are annealed to ensure alloying with Si-II 1009 and forming a good contact on SiO2-III 1010. The electrical contact to biosensor electrode 1015 using 999 PSV is further isolated from other biosensor electrodes (not shown) by creating an isolation region shown by etched regions 1013. It should also be appreciated that the geometry of etched region may have a cylindrical or rectangular cross-section, when viewed from the top or bottom side. In addition, an oxide or insulator layer 1014 is grown on exposed Si-II layer 1009 and Si-III 996 to isolate them from other PSVs. Although it is not shown, the etched region 1013 can be filled with undoped amorphous Si film like layer 1004 to obtain planarization.

It should be appreciated that in the embodiment disclosed above, the sub-chip#2 1016 fits in the recessed region of the SOI substrate 998 (serving as sub-chip#3 where the biosensor may be realized—see one electrode 1015). On the sub-chip#2 1016 side, the device is sealed using a gold fence 1018 which in turn is realized on a gold-silicon eutectic layer 997. Here, sub-chip#3 (hosting biosensors) is formed by layers 1015 which in turn are grown on layers 996, 1010, 1009. FIG. 10 describes another biosensor electrode 992 and is connected to subchip#2 1016 via another PSV 995. PSV 995 has Ohmic contact 994 and gold interconnect 993. The biosensor electrode 992 is isolated by etched region 991 which is surrounded by oxide layer 990 for passivation.

Figure 11A:
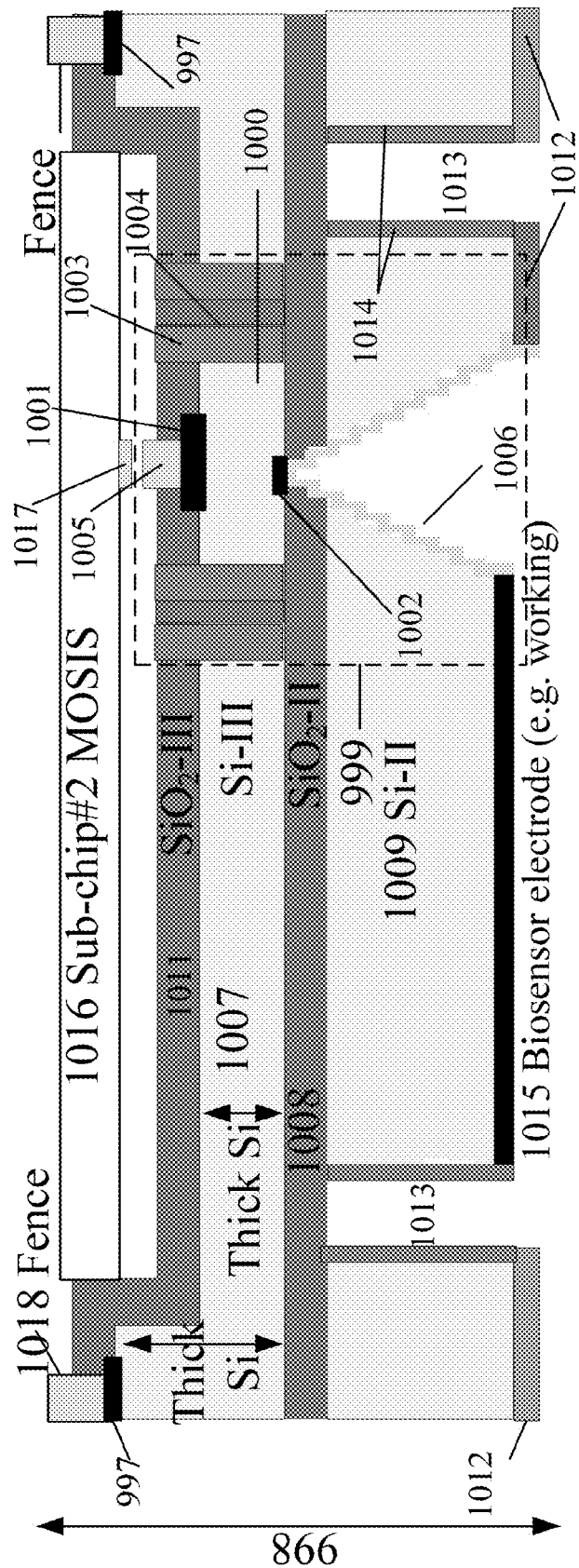
FIG. 11A is a cross-sectional schematic showing a Si pillar serving as partial silicon via (PSV) realized on a SOI substrate with additional $SiO_2$ layers.

Referring to FIG. 11A, a cross-sectional schematic showing an Si pillar that is serving as a PSV realized on a SOI substrate with no additional $SiO_2$ and poly Si layers (as shown in FIG. 10) are described. In this embodiment, only an SOI wafer is used and no poly Si layer is needed. The biosensor electrode 1015 is electrically connected to subchip #2 1016 pad 1017 using partial Si Via 999 without exposing the electronics of 1016 to body fluids to which the biosensor working electrode 1015 is exposed. Si vias are created by an electrically isolated Si pillar 1000 by insulating oxide ($SiO_2$) 1003 all around the pillar. The Si pillar 1000 is deposited with Ohmic contact 1001 on one side (the Sub-chip#2 side), and 1002 contact from the other side (biosensor side). The Ohmic contacts are in turn contacted by metal pads 1005 and 1006, where the regions 1005 and 1006 are deposited by etching SiO2 1008 and Si 1009 layers. Generally the width of an etched region is quite smaller than the Si pillar 1000, maintaining the mechanical robustness of the pillar and PSV. The oxide layer 1003 is grown on a Si layer 1007 surrounding the etched region separating the pillar 1000. The etched region isolating the pillar 1000 is filled with undoped amorphous Si film 1004 to enhance the robustness of the pillar 1000. The Si layer 1007 is shown thinner in the part which accommodates sub-chip#2 1016 and a thicker part where silicon-gold eutectic layer 997 and gold perimeter fence 1018 is formed.

The Ohmic contact 1001 is deposited with a gold pad 1005 and the Ohmic contact 1002 is deposited with a gold thin film 1006 to make electrical connections. Ohmic contact 1002 is created by etching SiO2 layer 1008 which surrounds it. The gold thin film 1006 is deposited and alloyed (via eutectic formation) on Si layer 1009. The SiO2 layer 1012 isolates the biosensor electrodes from each other (the other electrodes are not shown) and the gold layer may have a thin chrome (Cr) layer for adhesion on SiO2 films. The thin films are annealed to ensure alloying with Si and forming a good contact on SiO2. The electrical contact to biosensor electrode using PSV 999 is further isolated from other biosensor electrodes (not shown) by creating an isolation region shown by etched regions 1013. It should be appreciated that the geometry of the etched region may have cylindrical or rectangular cross-section, when viewed from the top or bottom side. In addition, oxide or insulator layer 1014 is grown on exposed Si layer 1009 to isolate them from other PSVs. Although it is not shown, the etched region 1013 can be filled with undoped amorphous Si film like layer 1004 to obtain planarization.

Figure 11B:
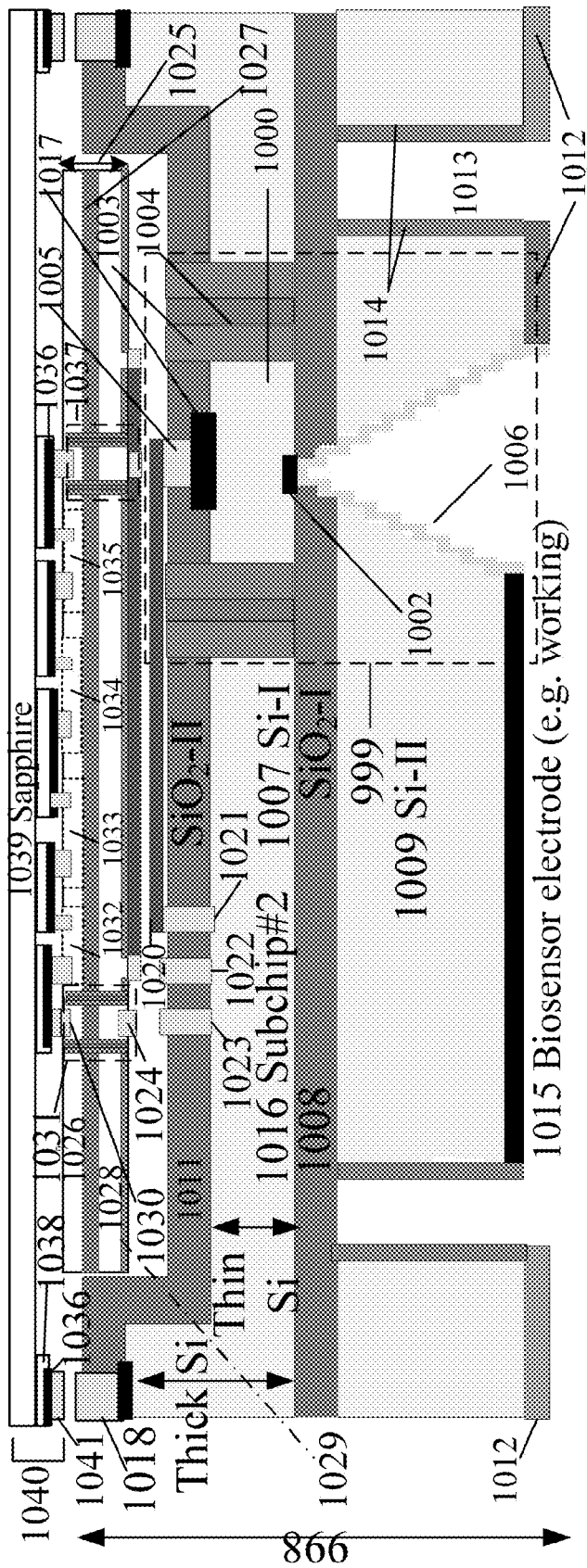
FIG. 11B is a cross-sectional schematic showing a Si pillar serving as partial silicon via (PSV) realized on a SOI substrate (with no additional $SiO_2$ and poly Si layers).

Referring to FIG. 11B another embodiment in which electronic devices and circuits are realized in the first Si layer 1007 is shown. In this embodiment, devices and circuits hosted on subchip #2 1016 may be fabricated in the Si layer 1007 using integrated processing methods. The bonding pad 1005 to silicon pillar 1000 (forming the PSV 999) is electrically connected via an electrical interconnect 1020 to a pad 1021 on subchip #2 1016. Other pads 1022 and 1023 are also shown. These pads are connected to other biosensor electrodes and are realized similarly to working electrode 1015 using partial Si vias 1031, or connected to bonding pads implemented on subchip#1 1025 which is realized on another SOI wafer with first Si 1026, first oxide 1027 and second silicon 1028 and third oxide layer 1029. As shown, the pad 1023 is interfaced with pad 1024 on subchip #1 (1025). The pads are envisioned to be having gold bumps to ensure mechanical and electrical robustness. In this embodiment, pad 1024 is connected to pad 1030 using partial silicon via 1031 which is similar in construction to PSV 999. Another PSV 1037 realized on 1025 SOI substrate is shown to provide a second electrical connection which may be connected to devices on subchip #2 or subchip#3 (biosensor chip).

First silicon layer 1026 in subchip#1 1025 is shown as hosting four (4) devices (1032, 1033, 1034, 1035), that are isolated from each other, and each having two electrode pads/bumps. These p-n devices may represent solar cells which are connected in series, wherein the electrical connection may be enabled using wire bonds or as shown, by electrical interconnection using patterned gold layer 1036 (which forms an eutectic and a thin gold layer for the gold fence 1041) deposited on Si thin film 1038 which in turn is deposited on a substrate 1039 which serves as a cover plate, permitting transmission of light in and out of the devices located on subchip#1 1025 and/or SOI substrate 998 comprising subchip 2 1016 devices, and biosensors. An example of this assembly 1040 comprising a thin silicon film 1038 on a sapphire substrate 1039 (silicon-on sapphire, SOS) with a patterned fence 1041 formed on 1036 is shown. The adhesion of Si to sapphire is quite robust. Au thin films forms eutectic to silicon where gold pads or bumps can be realized. The gold fence shown as 1041 is envisioned to seal the SOS cover substrate. In this scheme, subchip#1 1025 is configured to fit in the recessed region corresponding to thin Si region over subchip#2 1016. In another embodiment, through silicon vias may be used to electrically interconnect pads like 1023 on subchip #2 to pads like 1030 on subchip#1 (1025). Thus, biosensor subchip#3, subchip#2, and subchip#1 can now be electrically connected using PSVs and PSV and TSV combinations.

Figure 12:
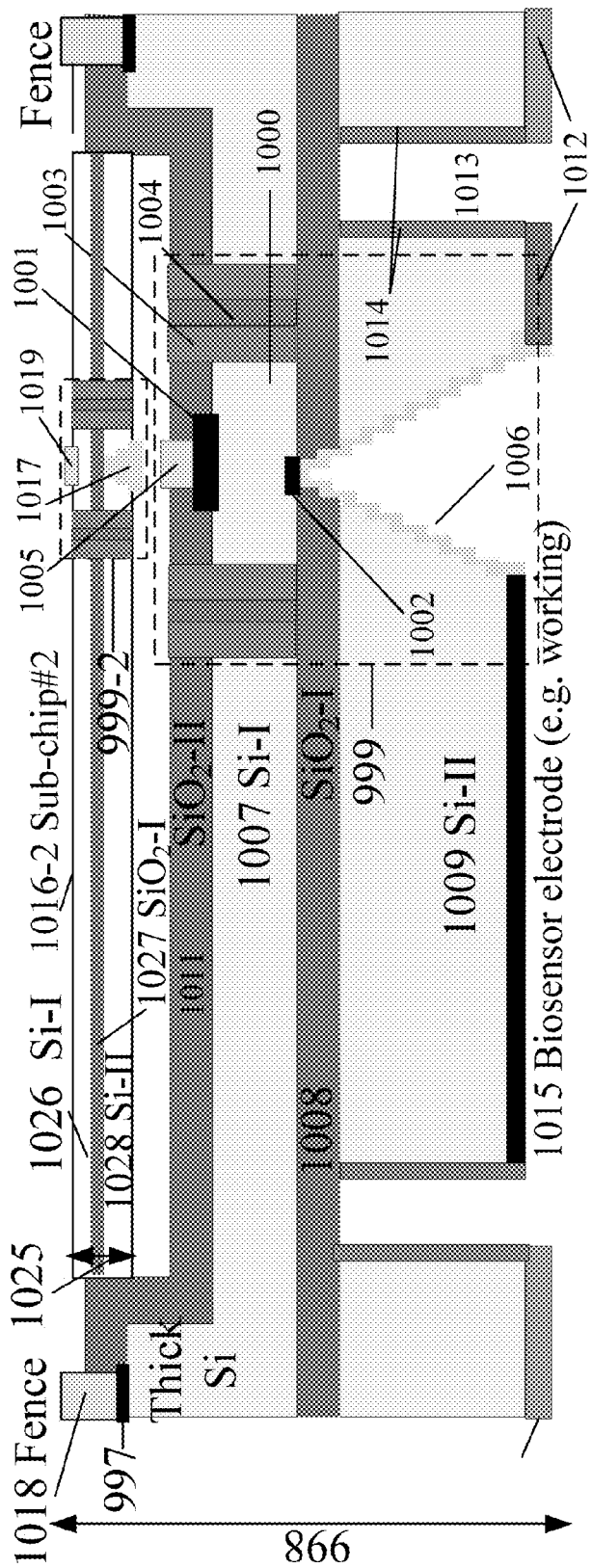
FIG. 12 is a cross-sectional schematic showing two levels of Si pillar serving as PSVs realized on two SOI substrates.

Referring to FIG. 12, a cross-sectional schematic of two sets of stacked PSVs (999 and 999-2) is shown connecting subchip#2 1016 realized on another SOI substrate 1025 having devices on Si-I layer 1026 and Si-II layer 1028 separated by oxide 1027 SiO2-I. The pad 1019 is realized on Si-I layer 1026 and pad 1017 connects to biosensor electrode 1015 via PSV 999. The SOI 1025 fits in the thin Si region Si-I 1007 on 998.

Figure 13:
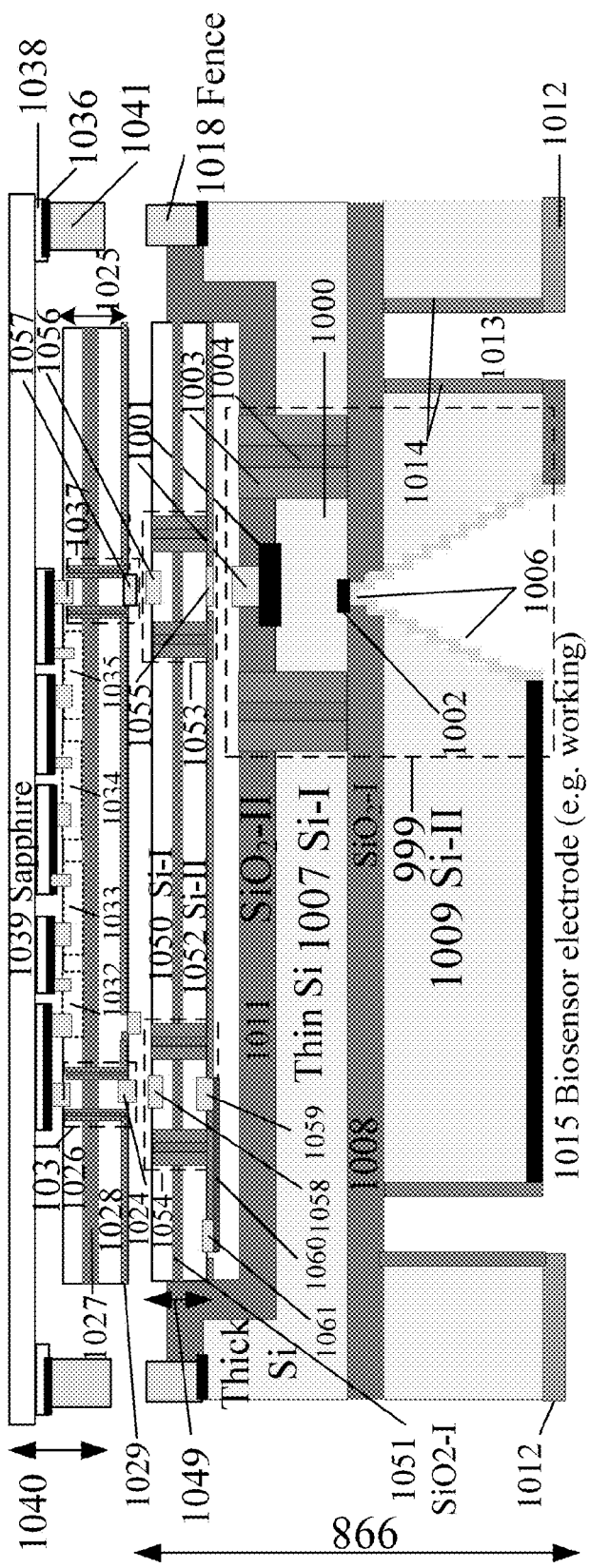
FIG. 13 is a hermetically sealed structure that uses stacked SOI substrates incorporating partial silicon vias (PSVs) interconnecting various chips sealed with a cover silicon-on-sapphire substrate.

Referring to FIG. 13, three SOI substrates (998, 1025 and 1049) that embody partial Si vias for interconnections with a cover substrate 1040 which may be comprised of silicon-on-sapphire (SOS) or silicon on quartz are shown. The cover substrate 1040 and subchip#1 1025 layer structure is shown in FIG. 11B. The devices on subchip#2 1049 are shown electrically connected to subchip#1 1025 via two PSVs 1053 and 1054. The entire assembly is shown hermetically sealed using a cover 1040 which may be comprised of a silicon-on-sapphire wafer with sapphire 1039 as the base on which Si layer 1038 is deposited. The Si layer 1038 is patterned to form a gold fence 1041 using gold-Si eutectic layer 1036. Subchip#2 1049 is realized on a SOI substrate that may be comprised of silicon Si-I 1050, SiO2-I 1051, and Si-II 1052. Subchip#1 1025 is connected to biosensor electrode 1015 via PSV 1053. Pad 1055 on PSV 1053 is connected to pad 1001. Pad 1056 is connected to pad 1057 on subchip#1 1025. PSV 1054 pad 1058 is connected to pad 1024 on subchip#1 1025. Pad 1059 on PSV 1054 is connected to pad 1061 located on subchip#2 through electrical interconnect 1060.

Figure 14:
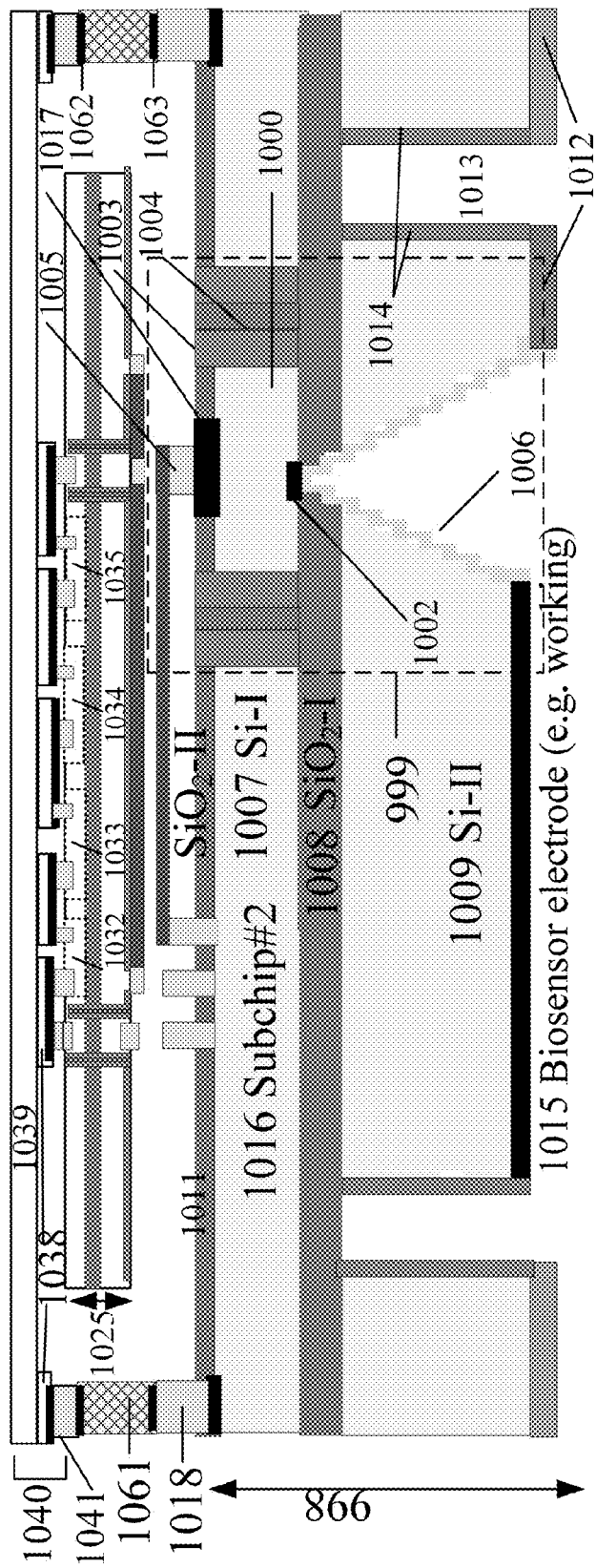
FIG. 14 is a hermetically sealed structure that uses stacked SOI substrates, incorporating a spacer substrate with part etched to provide space to accommodate chips bonded, sealed with a cover using silicon-on-sapphire substrate or wafer.

Referring to FIG. 14, a hermetically sealed structure using stacked SOI substrates, incorporating a spacer substrate 1061 which is etched to provide the space to accommodate subchip #1 1025 is provided. The spacer Si 1061 has gold-Si eutectic layers on both sides 1062 and 1063, wherein these gold layers may interface with respective gold fences 1018 and 1041. The assembly is sealed with a cover substrate 1040 which may be comprised of silicon-on-sapphire. It should be appreciated that the description of other layers can be found described herein relative to previous figures.

Figure 15:
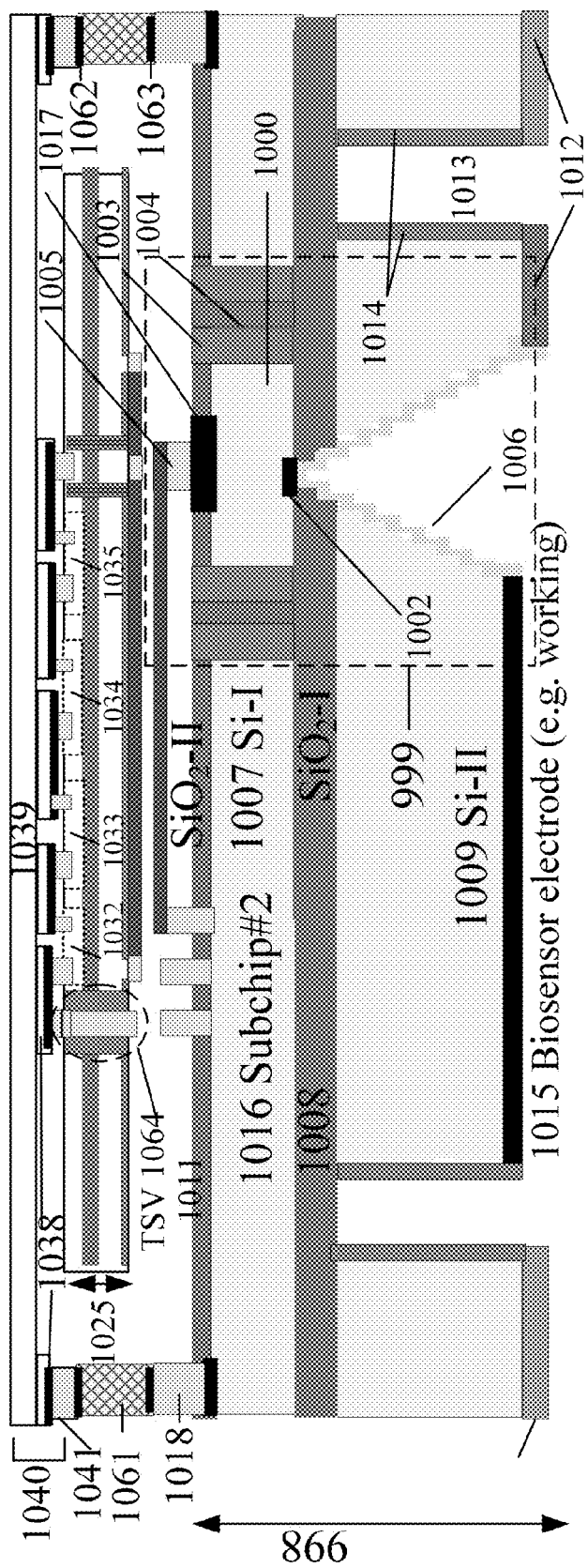
FIG. 15 is a hermetically sealed platform with partial silicon vias (PSVs) for surface device or biosensor interconnection and PSVs and through silicon vias (TSVs) for inside the package electrical connections or optical interconnects.

Referring to FIG. 15, a hermetically sealed platform with PSVs for biosensor interconnection and PSVs and TSVs for inside the package electrical connections or optical interconnects is shown and provided and includes a conventional through-silicon-via (TSV) 1064. It should be appreciated that variations of the above embodiments are envisioned for different applications including 3-dimensional stacking of Si chips, hybrid chips, solar cells, lasers and other devices. Moreover, it is contemplated that in some embodiments, germanium wafers can also be used in place of Si where gold-Ge eutectic may be formed. In addition to SiO2, other insulator materials like Si3N4, HfO2, Al2O3 etc. can be used as desired. GaAs and related InGaAs layered structures are also envisioned as subchip substrates.

This invention describes a hermetically sealed package which can be implanted in the body. The package comprise of stacked substrates where surface of one substrate hosts biosensors which are exposed to body fluids to monitor concentrations of substances selected from analytes, metabolites, and proteins, and body physiological parameters. The structure protects from body fluids devices that interface with the biosensor electrodes for electronic data processing, powering, and wireless communication. Biosensor electrodes are electrically connected to various electronic, optoelectronic, MEM devices using novel partial silicon vias (PSVs) that prevents leakage of body fluids. Various devices are located on different substrates which are stacked to save surface area. One of the substrate forms the cover plate which permits light for powering as well as sending receiving coded data including the analyte levels In another embodiment, the cover plate may be made of quartz and a thin film of patterned molybdenum (Mo) may be deposited where the perimeter seal is needed. Typically, Mo/quartz seals are known to withstand high temperature and vacuum conditions. This Mo film may then be covered with a thin film of Si, which may be physically deposited using sputtering or some other appropriate deposition method(s) as desired. Upon heat treatment, Mo forms MoSi, which provides superior adhesion between Si and Mo. As such, any remaining Si can be used to form an Si/Au eutectic substance, which can subsequently be used to form Au—Au seals. In still yet another embodiment, the top cover plate can be achieved using a polycrystalline Si film on substrates like glass, quartz, AlN, SiC, sapphire, ZnS, ZnO, etc. It is contemplated that various types of materials may be used to increase the operation temperature envelop of the platform to very high temperatures. These materials may include Molybdenum (Mo), Pt, Pd, Ni, etc, all of which form silicides which form a good bond like Au—Si eutectic.

It is contemplated that the article, implementation and/or fabrication of the invention may be embodied in forms that can be used for other applications than those disclosed herein. For example, various computing hardware and IC chips can be packaged within such miniaturized enclosures and directly attached onto devices that operate in a vacuum, under water, in corrosive liquids and gases, and other biological media. One such application may involve actuation of artificial muscles or various other microelectromechanical devices. The enclosure described herein can easily be adapted to house miniaturized pressure transducers at the site where PSVs are formed. Here, a thin Si film can serve as a diaphragm. In one embodiment, a traditional variable capacitor pressure transducer, a strain gauge type resistor, or a transistor element can be implemented from the inside part of this enclosure and be protected from the corrosive environment. Similarly, a chemFET device can be implemented on the exposed site and be interconnected with the passivated elelctronics through PSVs. Such devices, used in conjunction with remote powering and remote sensing can find a number of applications for nanosized robots together with diagnostic devices, smart dust sensors and satellite- or drone-operated distributed network of sensors.

Another application may include nanosized batteries in proximity to biological and other environments that cannot tolerate any leakage of battery electrolytes. Such nanosized packages incorporate battery electrolytes as well as cathodes and anodes within the enclosure, with the PSVs serving as the electrical contacts to the outside world (i.e. component external to the enclosure). Similarly, these or other PSVs can serve to charge these batteries by connecting them to biological fuel cells on the outside (i.e. external to the enclosure). In addition, these batteries can be remotely charged using photovoltaics cells, thermoelectric generators, RF powering sources etc. housed inside the enclosure.

Another application for such enclosures, particularly using high temperature materials such as MoSi, may involve situations that will expose the platform to high temperature environments, such as jet engines, automotive catalytic convertors, rockets, geothermal exploration, space crafts, nuclear environments, etc. Here, thermoelectric, photovoltaics and/or electromechanical sources can be also housed within the enclosure to protect them from the harmful effects of high temperatures and radiation. These devices can be used to power the devices within these enclosures. In still yet another application, PSV technology can be used to facilitate 3D integration of multiple IC chips. Here, the PSV technology is also complementary with liquid cooling using corrosive liquids like sea water.

In accordance with the present invention, the invention may be implemented as discussed in U.S. patent application Ser. No. 11/862,866 filed Sep. 27, 2007, the contents of which are incorporated herein in its entirety. For example, take the case of a glucose sensor. As disclosed in U.S. patent application Ser. No. 11/862,866, the integrated biosensor platform disclosed herein may be implanted subcutaneously in a subject such that the sensor elements sense characteristics of a body fluid of the subject. An external control unit located external to the body of the subject can communicate with the integrated biosensor platform via electromagnetic signals (such as via solar cells and/or photodetector ($PD_{SS}$)) to transmit and receive signals to and from the integrated biosensor platform.

The implementation and/or fabrication of the invention may be embodied in the form of a computer or controller implemented processes, in whole or in part. The invention may also be embodied in the form of computer program code containing instructions embodied in tangible media, such as floppy diskettes, CD-ROMs, hard drives, and/or any other computer-readable medium, wherein when the computer program code is loaded into and executed by a computer or controller, the computer or controller becomes an apparatus for practicing the invention. The invention can also be embodied in the form of computer program code, for example, whether stored in a storage medium, loaded into and/or executed by a computer or controller, or transmitted over some transmission medium, such as over electrical wiring or cabling, through fiber optics, or via electromagnetic radiation, wherein when the computer program code is loaded into and executed by a computer or a controller, the computer or controller becomes an apparatus for practicing the invention. When implemented on a general-purpose microprocessor the computer program code segments may configure the microprocessor to create specific logic circuits.

While the invention has been described with reference to an exemplary embodiment, it will be understood by those skilled in the art that various changes, omissions and/or additions may be made and equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

We claim:

1. A device, comprising:
  a layered structure in Si configured to form Si Vias for hermetically sealed electrical connectivity between two sets of devices, which are realized on at least two Si layers of a Si-on-insulator substrate,
  wherein the Si-on-insulator substrate is comprised of a first Si layer and a second Si layer separated by a first SiO2 layer serving as an insulator,
    wherein the first Si layer has on it a deposited second insulator film selected from SiO2, SiN, HfO2, and
    wherein Si pillars are created in the first Si layer by etching regions surrounding the Si pillars, wherein the Si pillars are supported by a first oxide layer and the second Si layer,
    wherein the exposed surface of the Si pillars and surrounding surface of the first Si layer are deposited with thin oxide layer selected from SiO2, HfO2, Si3N4, SiON, and
    wherein etched regions are filled with material selected from undoped amorphous Si, SiO2, HfO2, wherein the Si pillars have a top side and a bottom side, the bottom side interfaces with first oxide,
    wherein the second Si layer and the first oxide layer under the Si pillars are etched to expose the bottom side of the Si pillar in the first Si layer,
    wherein the exposed Si surface of bottom side of pillars are deposited with a metal providing Ohmic contact, wherein the metal is selected from gold, arsenic doped gold, aluminum, Pt, Pd, TiN, and TaN, and
    wherein the Ohmic contact is deposited with a metal pad selected from a biocompatible non-corrosive metal selected from Au, Pt, and Pd, and
    wherein the second Si layer side opposite to the first SiO2 layer is deposited with a passivation insulator layer selected from SiO2, HfO2, SiN, and Al2O3, and
    wherein the passivation insulator layer is patterned to expose second Si layer which is deposited with electrodes to form biosensors, electronic circuits, optoelectronic circuits, ultrasonic transducers and other devices that operate electrically,
    wherein the top side of the Si pillars are deposited with a metal providing Ohmic contact, and wherein the metal is selected from gold, arsenic doped gold, aluminum, Pt, Pd, TiN, and TaN, and
    wherein the Ohmic contact is deposited with a metal pad selected from Au, Pt, Pd, and wherein the metal pads on top side of Si pillars are connected to devices selected from electronic, photonic, optoelectronic, and micro-electro-mechanical realized in first Si layer.

2. The device of claim 1, wherein Si vias are formed for hermetically sealing electrical connectivity between two sets of devices, which are realized on at least three Si layers consisting of two Si layers comprised of Si-on-insulator substrate,
  wherein the Si-on-insulator substrate comprise of a first Si layer and a second Si layer separated by first SiO2 layer severing as an insulator,
  wherein the first Si layer has on it a deposited second insulator film selected from SiO2, SiN, and HfO2, and
  wherein the second Si layer is deposited with a third insulator layer selected from SiO2, SiN, and HfO2, and
  wherein the third insulator is deposited with a third Si layer selected from a poly-Si, and a poly Ge thin film, wherein the third Si layer is protected with a passivation insulator layer,
  wherein the passivation insulator layer is selected from SiO2, HfO2, SiN, and Al2O3,
  wherein the bottom side of the Si pillar in first Si layer is contacted by patterning and etching passivation insulator layer, third Si layer, third insulator layer, and second Si layer and first insulator layer,
  wherein the exposed Si surface of bottom side of pillars are deposited with a metal providing an Ohmic contact, wherein the metal is selected from gold, arsenic doped gold, aluminum, Pt, Pd, TiN, and TaN, and
  wherein the Ohmic contact is deposited with a metal pad selected from biocompatible non-corrosive metals selected from Au, Pt, and Pd, and
  wherein the passivation insulator layer is patterned to expose third Si layer which is deposited with electrodes to form biosensors, electronic circuits, optoelectronic circuits, ultrasonic transducers and other devices that operate electrically,
  wherein the top side of the Si pillars are deposited with a metal providing Ohmic contact, the metal is selected from gold, arsenic doped gold, aluminum, Pt, Pd, TiN, and TaN,
  wherein the Ohmic contact is deposited with a metal pad selected from Au, Pt, and Pd, and the metal pads on top side of Si pillars are connected to devices selected from electronic, photonic, optoelectronic, and micro-electro-mechanical realized in the first Si layer.

3. The device of claim 1, wherein the Si vias are configured to interconnect the biosensors and the electronic devices.

4. A hermetically sealed structure, comprising:
  at least two stacks of substrates, wherein the structure permits exposure of biosensor surfaces on which electrodes are realized to monitor concentrations of substances selected from analytes, metabolites, and proteins, and body physiological parameters,
  wherein the structure protects from body fluids devices that interface with the biosensor electrodes for electronic data processing, powering, and wireless communication, and
  wherein the devices are located on any of the substrates forming a stack,
  wherein biosensor electrodes are electrically, connected to the devices using partial silicon vias,
  wherein substrates forming the stack are selected from Si, Si-on-Insulator (SOI) and Silicon-on-sapphire, silicon-on-quartz,
  wherein the Si-on-insulator (SOI) substrate include a first Si layer and a second Si layer separated by a first SiO2 layer severing as an insulator, wherein the Si-on-sapphire (SOS) substrate includes a Si layer on a sapphire substrate, wherein the SOS substrate serves as a cover plate permitting light energy to be used to power the solar cells, located on other substrates forming the multi-stack structure, wherein the SOS substrate cover plate permitting coded light signals to communicate with receiver photodiodes located on the Si film on the SOS or other substrates, wherein the cover plate substrate having a gold film on the Si thin film forming an eutectic, wherein the thin film having a perimeter fence formed by gold bump layer, wherein the substrate hosting the biosensor electrodes includes on its other face a perimeter gold fence formed on the Si—Au eutectic thin film, wherein the biosensor hosting substrate and the cover plate substrate heremetically seal the vertical stack.

5. The hermetically sealed structure of claim 4, further comprising a Si frame wafer with perimeter fence matching the top cover wafer and bottom biosensor substrate, wherein the stack forms a sealed structure, and wherein the Si frame substrate being hollow in the middle provides space to bond pads of bottom and top substrates.

* * * * *